US008076350B2

(12) United States Patent
Ji et al.

(10) Patent No.: US 8,076,350 B2
(45) Date of Patent: Dec. 13, 2011

(54) SPIROCYCLIC AZAADAMANTANE DERIVATIVES AND METHODS OF USE

(75) Inventors: Jianguo Ji, Libertyville, IL (US);
Michael R. Schrimpf, Grayslake, IL (US); Kevin B. Sippy, Antioch, IL (US);
Tao Li, Grayslake, IL (US); Chih-Hung Lee, Vernon Hills, IL (US)

(73) Assignee: Abbott Laboratories, Abbott Park, IL (US)

( * ) Notice: Subject to any disclaimer, the term of this patent is extended or adjusted under 35 U.S.C. 154(b) by 1054 days.

(21) Appl. No.: 11/943,045

(22) Filed: Nov. 20, 2007

(65) Prior Publication Data

US 2008/0153860 A1    Jun. 26, 2008

Related U.S. Application Data

(60) Provisional application No. 60/876,668, filed on Dec. 22, 2006.

(51) Int. Cl.
*A61K 31/438* (2006.01)
*A61K 31/439* (2006.01)
*C07D 498/10* (2006.01)
*C07D 498/12* (2006.01)

(52) U.S. Cl. ......................................... 514/278; 546/18
(58) Field of Classification Search .................... 546/18; 514/278
See application file for complete search history.

(56) References Cited

U.S. PATENT DOCUMENTS

2002/0045617 A1    4/2002    Grewal et al.

FOREIGN PATENT DOCUMENTS

| EP | 1359152 | 5/2003 |
|---|---|---|
| WO | 0181347 | 11/2001 |
| WO | 2004064836 | 8/2004 |
| WO | 2005028477 | 3/2005 |
| WO | 2006005233 | 6/2006 |
| WO | 2007038058 | 4/2007 |

OTHER PUBLICATIONS

Adams, C., et al., Developmental Brain Research, 139: 175-187 (2002).
Adler, L. E., et al., Schizophrenia Bulletin, 24: 189-202 (1998).
Becker, D.P., et al, Synthesis, 1080-1082 (1992).
Bitner R., et al., Soc. Neuroscience, Abstract 325.6 (2006).
Buck, E., et al., Org. Lett., 4: 1623-1626 (2002).
Charles, M., et al, Org. Lett., 7(18): 3965-3968 (2005).
Cordero-Erausquin, M., et al., PNAS, 98: 2803-2807 (2001).
Eliel, E., et al., "Stereochemistry of Organic Compounds", John Wiley & Sons, Inc., New York, NY, Table of Contents (1994).
Falk, L., et al., Developmental Brain Research, 142: 151-160 (2003).
Friedman, J., et al., Biol. Psychiatry, 51: 349-357 (2002).
Furniss, et al., Vogel's Textbook of Practical Organic Chemistry, 5th edition, Longman Scientific & Technical, Essex CM20 SJE, England, Table of Contents (1989).
Greene, T., et al., Protective Groups in Organic Synthesis, 3rd edition, John Wiley & Sons, New York, Table of Contents (1999).
Higuchi, T., et al., Prodrugs as Novel Delivery Systems, vol. 14 of the A.C.S. Symposium Series, Washington D.C., Table of Contents (1975).
Roche, E., Bioreversible Carriers in Drug Design, American Pharmaceutical Association and Pergamon Press, New York, NY, Table of Contents (1987).
Heeschen, C., et al., The Journal of Clinical Investigation, 110(4): 527-536 (2002).
Heeschen, C., et al., Nature Medicine, 7(7): 833-839 (2001).
IUPAC 1974 Recommendations for Section E, Fundamental stereochemistry, Pure Appl. Chem., 45: 13-30 ( 1974).
Jacobi, J., et al., American Journal of Pathology, 161(1): 97-104 (2002).
Jonnala, R., et al., J. Neurosci. Res., 66: 565-572 (2001).
Kesel, A., Current Medicinal Chemistry, 12(18): 2095-2162 (2005).
Kihara, T., et al., J. Biol. Chem., 276: 13541-13546 (2001).
Leonard, S., et al., Eur. J. Pharmacol., 393: 237-242 (2000).
Levin, E., J. Neurobiol., 53: 633-640 (2002).
Liu, Q., et al., PNAS, 98: 4734-4739 (2001).
Pabreza, L., et al., Molecular Pharmacology, 39: 9-12 (1990).
Paterson, D., et al., Progress in Neurobiology, 61: 75-111 (2000).
Prescott, Ed., Methods in Cell Biology, Academic Press, New York, NY, p. 33 et seq. (1976).
Radek R., et al., Psychopharmacology, 187: 47-55( 2006).
Rowley, M., et al., Journal of Med. Chem., 44(4): 477-501 (2001).
Sawa, A., et al., Mol. Med., 9: 3-9 (2003).
Shimohama, S., et al., Brain Res., 779: 359-363 (1998).
Son, J., et al., Biology of Reproduction, 68: 1348-1353 (2003).
Stetter, H., et al., Chemische Berichte, 105: 2773-2779 (1972).
Stevens, K., et al., Psychopharmacology, 136: 320-327 (1998).
Tsuneki, H., et al., J. Physiol., 547: 169-179 (2003).
Wang, H., et al., 421: 3984-388 (2003).
PCT International Search Report, PCT Application No. PCT/US2007/085566, mailing date Mar. 20, 2008.
Wilens, T., et al., American Journal of Psychiatry 156(12): 1931-1937 (1999).

*Primary Examiner* — Rita Desai
(74) *Attorney, Agent, or Firm* — Lisa V. Mueller; Michael Best & Friedrich LLP

(57) ABSTRACT

The invention relates to compounds that are spirocyclic azaadamantane derivatives derivatives, particularly spirocyclic azaadamantanyl ether or amine derivatives, compositions comprising such compounds, methods of using such compounds and compositions, processes for preparing such compounds, and intermediates obtained during such processes.

6 Claims, No Drawings

SPIROCYCLIC AZAADAMANTANE DERIVATIVES AND METHODS OF USE

CROSS-REFERENCE SECTION TO RELATED APPLICATIONS

This application claims the benefit of U.S. Provisional Patent Application No. 60/876,668, filed Dec. 22, 2006, which is hereby incorporated by reference in its entirety.

BACKGROUND OF THE INVENTION

1. Technical Field

The invention relates to spirocyclic azaadamantane derivatives, and more particularly spirocyclic azaadamantanyl ether or amine derivatives, compositions comprising such compounds methods of preventing or treating conditions and disorders using such compounds and compositions, process for preparing such compounds, and intermediates obtained during such processes.

2. Description of Related Technology

Nicotinic acetylcholine receptors (nAChRs) are widely distributed throughout the central (CNS) and peripheral (PNS) nervous systems. Such receptors play an important role in regulating CNS function, particularly by modulating release of a wide range of neurotransmitters, including, but not necessarily limited to, acetylcholine, norepinephrine, dopamine, serotonin, and GABA. Consequently, nicotinic receptors mediate a very wide range of physiological effects, and have been targeted for therapeutic treatment of disorders relating to cognitive function, learning and memory, neurodegeneration, pain, inflammation, psychosis, sensory gating, mood, and emotion, among other conditions.

Many subtypes of the nAChR exist in the CNS and periphery. Each subtype has a different effect on regulating the overall physiological function. Typically, nAChRs are ion channels that are constructed from a pentameric assembly of subunit proteins. At least 12 subunit proteins. $\alpha 2$-$\alpha 10$ and $\beta 2$-$\beta 4$, have been identified in neuronal tissue. These subunits provide for a great variety of homomeric and heteromeric combinations that account for the diverse receptor subtypes. For example, the predominant receptor that is responsible for high affinity binding of nicotine in brain tissue has composition $(\alpha 4)_2(\beta 2)_3$ (the $\alpha 4\beta 2$ subtype), while another major population of receptors is comprised of homomeric $(\alpha 7)_5$ (the $\alpha 7$ subtype) receptors.

Certain compounds, like the plant alkaloid nicotine, interact with all subtypes of the nAChRs, accounting for the profound physiological effects of this compound. While nicotine has been demonstrated to have many beneficial properties, not all of the effects mediated by nicotine are desirable. For example, nicotine exerts gastrointestinal and cardiovascular side effects that interfere at therapeutic doses, and its addictive nature and acute toxicity are well-known. Ligands that are selective for interaction with only certain subtypes of the nAChR offer potential for achieving beneficial therapeutic effects with an improved margin for safety.

The $\alpha 7$ and $\alpha 4\beta 2$ nAChRs have been shown to play a significant role in enhancing cognitive function, including aspects of learning, memory and attention (Levin, E. D., J. Neurobiol. 53: 633-640, 2002). For example, $\alpha 7$ nAChRs have been linked to conditions and disorders related to attention deficit disorder, attention deficit hyperactivity disorder (ADHD), schizophrenia, Alzheimer's disease (AD), mild cognitive impairment, senile dementia, dementia associated with Lewy bodies, dementia associated with Down's syndrome, AIDS dementia, and Pick's Disease, as well as inflammation. The $\alpha 4\beta 2$ receptor subtype is implicated in attention, cognition, epilepsy, and pain control (Paterson and Norberg. *Progress in Neurobiology,* 61 75-111, 2000).

The activity at both $\alpha 7$ and $\alpha 4\beta 2$ nAChRs can be modified or regulated by the administration of subtype selective nAChR ligands. The ligands can exhibit antagonist, agonist, or partial agonist properties. Compounds that function as positive allosteric modulators are also known.

Although some compounds that nonselectively demonstrate activity at a range of nicotinic receptor subtypes including the $\alpha 4\beta 2$ and $\alpha 7$ nAChRs are known, it would be beneficial to provide new compounds that demonstrate selectivity for $\alpha 7$-containing neuronal nAChRs, $\alpha 4\beta 2$ nAChRs, or both $\alpha 7$ and $\alpha 4\beta 2$ nAChRs compared to other subtypes to provide further candidates for drug development.

SUMMARY OF THE INVENTION

The invention is directed to spirocyclic azaadamantane derivatives, compositions comprising such compounds, processes for preparing such compounds, and intermediates obtained during such processes. More particularly, the invention relates to spirocyclic azaadamantanyl ether or amine compounds and related methods and processes thereof.

One aspect of the invention relates to a compound of formula (I)

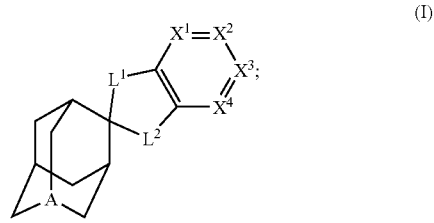

or a pharmaceutically acceptable salt or prodrug thereof, wherein

A is N or $N^+$—$O^-$;
$X^1$ is $CR^{x1}$ or N;
$X^2$ is $CR^{x2}$ or N;
$X^3$ is $CR^{x3}$ or N;
$X^4$ is $CR^{x4}$ or N;
$L^1$ and $L^2$ are each independently —O— and —$NR^b$; —$R^cC$=O, or $C_1$-$C_3$ alkyl;
$R^{x1}$, $R^{x2}$, $R^{x3}$ and $R^{x4}$ are each independently H, alkyl, aryl cyclic alkyl, halogen, halo alkyl, heteroaryl, $OR^b$, $NR^dR^c$, $COR^b$, CN, $CO_2R^b$, or $CONR^dR^e$;
$R^b$, $R^d$ and $R^e$ are independently H, alkyl, aryl, alkylcarbonyl, alkoxylcarbonyl, or heteroaryl; and
$R^c$ is absent or $R^c$ is —O—, or —$NR^b$.

Another aspect of the invention relates to pharmaceutical compositions comprising compounds of the invention. Such compositions can be administered in accordance with a method of the invention, typically as part of a therapeutic regimen for treatment or prevention of conditions and disorders related to nAChR activity, and more particularly $\alpha 7$ nAChR activity, $\alpha 4\beta 2$ nAChR activity, or both $\alpha 7$ nAChR activity and $\alpha 4\beta 2$ nAChR activity.

Yet another aspect of the invention relates to a method of modulating both $\alpha 7$ and $\alpha 4\beta 2$ nAChR activity. The method is useful for treating, preventing or both treating and preventing conditions and disorders related to both $\alpha 7$ and $\alpha 4\beta 2$ nAChR activity, particularly in mammals.

A further aspect of the invention relates to a method of selectively modulating nAChR activity, for example α7 nAChR activity. The method is useful for treating, preventing or both treating and preventing conditions and disorders related to α7 nAChR activity in mammals. More particularly, the method is useful for conditions and disorders related to attention deficit disorder, attention deficit hyperactivity disorder (ADHD), Alzheimer's disease (AD), schizophrenia, mild cognitive impairment, age-associated memory impairment (AAMI), senile dementia, AIDS dementia, Pick's Disease, dementia associated with Lewy bodies, dementia associated with Doings syndrome, schizophrenia, amyotrophic lateral sclerosis, Huntington's disease, diminished CNS function associated with traumatic brain injury, acute pain, post-surgical pain, chronic pain, inflammatory pain, neuropathic pain, infertility, lack of circulation, need for new blood vessel growth associated with wound healing, more particularly circulation around a vascular occlusion, need for new blood vessel growth associated with vascularization of skin grafts, ischemia, inflammation, sepsis, wound healing, and other complications associated with diabetes, among other systemic and neuroimmunomodulatory activities.

A method of selectively modulating nAChR activity, for example α4β2 nAChR activity, also is contemplated.

The compounds, compositions comprising the compounds, methods for using the compounds, and processes for preparing the compounds, as well as intermediates obtained in such processes, are further described herein.

DETAILED DESCRIPTION OF THE INVENTION

Definition of Terms

As used throughout this specification and the appended claims, the following terms have the following meanings:

The term "alkenyl" as used herein, means a straight or branched chain hydrocarbon containing from 2 to 10 carbons and containing at least one carbon-carbon double bond formed by the removal of two hydrogens. Representative examples of alkenyl include but are not limited to ethenyl. 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of from 2 to 10 carbon atoms containing at least one double bond. Representative examples of alkenylene include, but are not limited to, —CH=CH—, —CH=CH$_2$CH$_2$—, and —CH=C(CH$_3$)CH$_2$—.

The term "alkenyloxy" as used herein, means an alkenyl group, as defined herein, appended to the parent molecular moiety through an oxygen atom. Representative examples of alkenyloxy include, but are not limited to, allyloxy, 2-butenyloxy and 3-butenyloxy.

The term "alkoxy" as used herein, means an alkyl group, as defined herein, appended to the parent molecular moiety through an oxygen atom. Representative examples of alkoxy include, but are not limited to methoxy, ethoxy, propoxy, 2-propoxy, butoxy, tert-butoxy, pentyloxy, and hexyloxy.

The term "alkoxyalkoxy" as used herein, means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy. 2-methoxyethoxy, and methoxymethoxy.

The term "alkoxyalkoxyalkyl" as used herein, means an alkoxyalkoxy group, as defined herein, appended to the parent molecular moiety through an alkyl group, as defined herein. Representative examples of alkoxyalkoxyalkyl include, but are not limited to, tert-butoxymethoxymethyl, ethoxymethoxymethyl, (2-methoxyethoxy)methyl, and 2-(2-methoxyethoxy)ethyl.

The term "alkoxyalkyl" as used herein, means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein, means an alkoxy group, as defined herein, appended to the parent molecular moiety through a carbonyl group, as defined herein. Representative examples or alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, appended to the parent molecular moiety through an alkyl group, as defined herein. Representative examples of alkoxycarbonylalkyl include, but are not limited to, 3-methoxycarbonylpropyl, 4-ethoxycarbonylbutyl, and 2-tert-butoxycarbonylethyl.

The term "alkoxysulfonyl" as used herein, means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonylalkyl" as used herein, means an alkylcarbonyl group, as defined herein, appended to the parent molecular moiety through an alkyl group, as defined herein. Representative examples of alkylcarbonylalkyl include, but are not limited to, 2-oxopropyl, 3,3-dimethyl-2-oxopropyl, 3-oxobutyl, and 3-oxopentyl.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylene" means a divalent group derived from a straight or branched chain hydrocarbon of from 1 to 10 carbon atoms. Representative examples of alkylene include, but are not limited to, —CH$_2$—, —CH(CH$_3$)—, —C(CH$_3$)$_2$—, —CH$_2$CH$_2$—, —CH$_2$CH$_2$CH$_2$—, —CH$_2$CH—CH$_2$CH$_2$—, and —CH$_2$CH(CH$_3$)CH$_2$—.

The term "alkylsulfinyl" as used herein, means an alkyl group, as defined herein, appended to the parent molecular moiety through a sulfinyl group, as defined herein. Representative examples of alkylsulfinyl include, but are not limited to, methylsulfinyl and ethylsulfinyl.

The term "alkylsulfinylalkyl" as used herein, means an alkylsulfinyl group, as defined herein, appended to the parent molecular moiety through an alkyl group, as defined herein, Representative examples of alkylsulfinylalkyl include, but are not limited to methylsulfinylmethyl and ethylsulfinylmethyl.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylsulfonylalkyl" as used herein, means an alkylsulfonyl group, as defined herein, appended to the parent molecular moiety through an alkyl group, as defined herein. Representative examples of alkylsulfonylalkyl include, but are not limited to, methylsulfonylmethyl and ethylsulfonylmethyl.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkylthioalkyl" as used herein, means an alkylthio group, as defined herein, appended to the parent molecular moiety through an alkyl group, as defined herein. Representative examples of alkylthioalkyl include, but are not limited, methylthiomethyl and 2-(ethylthio)ethyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "alkynylene" means a divalent group derived from a straight or branched chain hydrocarbon of from 2 to 10 carbon atoms containing at least one triple bond. Representative examples of alkynylene include, but are not limited to, —C≡C—, —CH$_2$C≡C—, —CH(CH$_3$)CH$_2$C≡C—, —C≡CCH$_2$—, and —C≡CCH(CH$_3$)CH$_2$—.

The term "alkynyloxy" as used herein, means an alkynyl group, as defined herein, appended to the parent molecular moiety through an oxygen atom. Representative examples of alkynyloxy include, but are not limited to, 2-propynyloxy and 2-butynyloxy.

The term "aryl," as used herein, means phenyl, a bicyclic aryl or a tricyclic aryl. The bicyclic aryl is naphthyl, a phenyl fused to a cycloalkyl, or a phenyl fused to a cycloalkenyl. Representative examples of the bicyclic aryl include, but are not limited to, dihydroindenyl, indenyl, naphthyl, dihydronaphthalenyl, and tetrahydronaphthalenyl. The tricyclic aryl is anthracene or phenanthrene, or a bicyclic aryl fused to a cycloalkyl, or a bicyclic aryl fused to a cycloalkenyl, or a bicyclic aryl fused to a phenyl. Representative examples of tricyclic aryl ring include, but are not limited to, azulenyl, dihydroanthracenyl, fluorenyl, and tetrahydrophenanthrenyl.

The aryl groups of this invention can be substituted with 1, 2, 3, 4 or 5 substituents independently selected from alkenyl, alkoxy, alkoxyalkoxy, alkoxyalkoxyalkyl, alkoxyalkyl, alkoxycarbonyl, alkoxycarbonylalkyl, alkyl, alkylcarbonyl, alkylcarbonylalkyl, alkylcarbonyloxy, alkylsulfinyl, alkylsulfinylalkyl, alkylsulfonyl, alkylsulfonylalkyl, alkylthio, alkylthioalkyl, alkynyl, carboxy, carboxyalkyl, cyano, cyanoalkyl, formyl, formylalkyl, halogen, haloalkyl, hydroxy, hydroxyalkyl, mercapto, nitro, —NZ$_1$Z$_2$, and (NZ$_3$Z$_4$)carbonyl.

The term "arylalkoxy" as used herein, means an aryl group, as defined herein, appended to the parent molecular moiety through an alkoxy group, as defined herein. Representative examples of arylalkoxy include, but are not limited to, 2-phenylethoxy, 3-naphth-2-ylpropoxy, and 5-phenylpentyloxy.

The term "arylalkoxycarbonyl" as used herein, means an arylalkoxy group, as defined herein, appended to the parent molecular moiety through a carbonyl group, as defined herein. Representative examples of arylalkoxycarbonyl include, but are not limited to, benzyloxycarbonyl and naphth-2-ylmethoxycarbonyl.

The term "arylalkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "arylalkylthio" as used herein, means an arylalkyl group, as defined herein, appended to the parent molecular moiety through a sulfur atom. Representative examples of arylalkylthio include, but are not limited to, 2-phenylethylthio, 3-naphth-2-ylpropylthio, and 5-phenylpentylthio.

The term "arylcarbonyl" as used herein, means an aryl group, as defined herein, appended to the parent molecular moiety through a carbonyl group, as defined herein. Representative examples of arylcarbonyl include, but are not limited to, benzoyl and naphthoyl.

The term "aryloxy" as used herein, means an aryl group, as defined herein, appended to the parent molecular moiety through an oxygen atom. Representative examples of aryloxy include, but are not limited to, phenoxy, naphthyloxy, 3-bromophenoxy, 4-chlorophenoxy, 4-methylphenoxy, and 3,5-dimethoxyphenoxy.

The term "aryloxyalkyl" as used herein, means an aryloxy group, as defined herein, appended to the parent molecular moiety through an alkyl group, as defined herein. Representative examples of aryloxyalkyl include, but are not limited to, 2-phenoxyethyl, 3-naphth-2-yloxypropyl and 3-bromophenoxymethyl.

The term "arylthio" as used herein, means an aryl group as defined herein, appended to the parent molecular moiety through a sulfur atom. Representative examples of arylthio include, but are not limited to, phenylthio and 2-naphthylthio.

The term "arylthioalkyl" as used herein, means an arylthio group, as defined herein, appended to the parent molecular moiety through an alkyl group, as defined herein. Representative examples of arylthioalkyl include, but are not limited to, phenylthiomethyl, 2-naphth-2-ylthioethyl, and 5-phenylthiomethyl.

The term "azido" as used herein, means a —N$_3$ group.

The term "carbonyl" as used herein, means a —C(O)— group.

The term "carboxy" as used herein, means a —CO$_2$H group.

The term "carboxyalkyl" as used herein, means a carboxy group, as defined herein, appended to the parent molecular moiety through an alkyl group, as defined herein. Representative examples of carboxyalkyl include, but are not limited to, carboxymethyl, 2-carboxyethyl, and 3-carboxypropyl.

The term "cyano" as used herein, means a —CN group.

The term "cyanoalkyl" as used herein, means a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "cycloalkenyl" as used herein, means a cyclic hydrocarbon containing from 3 to 8 carbons and containing at least one carbon-carbon double bond formed by the removal of two hydrogens. Representative examples of cycloalkenyl include, but are not limited to, 2-cyclohexen-1-yl, 3-cyclohexen-1-yl. 2,4-cyclohexadien-1-yl and 3-cyclopenten-1-yl.

The term "cycloalkyl" as used herein, means a monocyclic, bicyclic, or tricyclic ring system. Monocyclic ring systems are exemplified by a saturated cyclic hydrocarbon group containing from 3 to 8 carbon atoms. Examples of monocyclic ring systems include cyclopropyl, cyclobutyl, cyclopentyl, cyclohexyl, cycloheptyl, and cyclooctyl. Bicyclic ring systems are exemplified by a bridged monocyclic ring system in which two adjacent or non-adjacent carbon atoms of the monocyclic ring are linked by an alkylene bridge of between one and three additional carbon atoms. Tricyclic ring systems are exemplified by a bicyclic ring system in which two non-adjacent carbon atoms of the bicyclic ring are linked by a bond or an alkylene bridge of between one and three carbon atoms. Representative examples of tricyclic-ring systems include, but are not limited to, tricyclo[3.3.1.0$^{3,7}$]nonane and tricyclo[3.3.1.1$^{3,7}$]decane (adamantane).

The cycloalkyl groups of the invention are optionally substituted with 1, 2, 3, 4 or 5 substituents selected from the group consisting of alkenyl, alkoxy, alkoxyalkoxy, alkoxyalkyl, alkoxycarbonyl, alkoxysulfonyl, alkyl, alkylcarbonyl, alkylcarbonyloxy, alkylsulfonyl, alkylthio, alkylthioalkyl, alkynyl, carboxy, cyano, formyl, haloalkoxy, haloalkyl, halogen, hydroxy, hydroxyalkyl, mercapto, oxo, —NZ$_1$Z$_2$, and (NZ$_3$Z$_4$)carbonyl.

The term "cycloalkylalkyl" as used herein, means a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "cycloalkylcarbonyl" as used herein, means cycloalkyl group, as defined herein, appended to the parent molecular moiety through a carbonyl group, as defined herein. Representative examples of cycloalkylcarbonyl include, but are not limited to, cyclopropylcarbonyl, 2-cyclobutylcarbonyl, and cyclohexylcarbonyl.

The term "cycloalkyloxy" as used herein, means cycloalkyl group, as defined herein, appended to the parent molecular moiety through an oxygen atom, as defined herein. Representative examples of cycloalkyloxy include, but are not limited to, cyclopropyloxy, cyclobutyloxy, cyclopentyloxy, cyclohexyloxy, cycloheptyloxy, and cyclooctyloxy.

The term "cycloalkylthio" as used herein, means cycloalkyl group, as defined herein, appended to the parent molecular moiety through a sulfur atom, as defined herein. Representative examples of cycloalkylthio include, but are not limited to, cyclopropylthio, cyclobutylthio, cyclopentylthio, cyclohexylthio, cycloheptylthio, and cyclooctylthio.

The term "ethylenedioxy" as used herein, means a —O(CH$_2$)$_2$O— group wherein the oxygen atoms of the ethylenedioxy group are attached to the parent molecular moiety through one carbon atom forming a 5 membered ring or the oxygen atoms of the ethylenedioxy group are attached to the parent molecular moiety through two adjacent carbon atoms forming a six membered ring.

The term "formyl" as used herein, means a —C(O)H group.

The term "formylalkyl" as used herein, means a formyl group, as defined herein, appended to the parent molecular moiety through an alkyl group, as defined herein. Representative examples of formylalkyl include, but are not limited to, formylmethyl and 2-formylethyl.

The term "halo" or "halogen" as used herein, means —Cl, —Br, —I or —F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl" as used herein, means a monocyclic heteroaryl or a bicyclic heteroaryl. The monocyclic heteroaryl is a 5 or 6 membered ring that contains at least one heteroatom selected from the group consisting of nitrogen, oxygen and sulfur. The 5 membered ring contains two double bonds and the 6 membered ring contains three double bonds. The 5 or 6 membered heteroaryl is connected to the parent molecular moiety through any carbon atom or any substitutable nitrogen atom contained within the heteroaryl, provided that proper valance is maintained. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, or a monocyclic heteroaryl fused to a cycloalkyl, or a monocyclic heteroaryl fused to a cycloalkenyl, or a monocyclic heteroaryl fused to a monocyclic heteroaryl. The bicyclic heteroaryl is connected to the parent molecular moiety through any carbon atom or any substitutable nitrogen atom contained within the bicyclic heteroaryl, provided that proper valance is maintained. Representative examples of bicyclic heteroaryl include, but are not limited to azaindolyl, benzimidazolyl, benzofuranyl, benzoxadiazolyl, benzoisoxazole, benzoisothiazole, benzooxazole, 1,3-benzothiazolyl, benzothiophenyl, cinnolinyl, furopyridine, indolyl, indazolyl, isobenzofuran, isoindolyl, isoquinolinyl, naphthyridinyl, oxazolopyridine, quinolinyl, quinoxalinyl and thienopyridinyl.

The heteroaryl groups of the invention are optionally substituted with 1, 2, 3 or 4 substituents independently selected from the group consisting of alkenyl, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, formyl, haloalkoxy, haloalkyl, halogen, hydroxy, hydroxyalkyl, mercapto, nitro, —NZ$_1$Z$_2$ and (NZ$_3$Z$_4$)carbonyl. Heteroaryl groups of the invention that are substituted with a hydroxyl group may be present as tautomers. The heteroaryl groups of the invention encompasses all tautomers including non-aromatic tautomers.

The term "heteroarylalkoxy" as used herein, means a heteroaryl group, as defined herein, appended to the parent molecular moiety through an alkoxy group, as defined herein. Representative examples or heteroarylalkoxy include, but are not limited to fur-3-ylmethoxy, 1H-imidazol-2-ylmethoxy, 1H-imidazol-4-ylmethoxy. 1-(pyridin-4-yl)ethoxy, pyridin-3-ylmethoxy, 6-chloropyridin-3-ylmethoxy, pyridin-4-ylmethoxy, (6-(trifluoromethyl)pyridin-3-yl)methoxy, (6-(cyano)pyridin-3-yl)methoxy, (2-(cyano)pyridin-4-yl)methoxy, (5-(cyano)pyridin-2-yl)methoxy, (2-(chloro)pyridin-4-yl)methoxy, pyrimidin-5-ylmethoxy, 2-(pyrimidin-2-yl)propoxy, thien-2-ylmethoxy, and thien-3-ylmethoxy.

The term "heteroarylalkyl" as used herein, means a heteroaryl, as defined herein, appended to the parent molecular moiety through an alkyl group, as defined herein. Representative examples of heteroarylalkyl include, but are not limited to, fur-3-ylmethyl, 1H-imidazol-2-ylmethyl, 1H-imidazol-4- ylmethyl, 1-(pyridin-4-yl)ethyl, pyridin-3-ylmethyl, 6-chloropyridin-3-ylmethyl, pyridin-4-ylmethyl, (6-(trifluoromethyl)pyridin-3-yl)methyl, (6-(cyano)pyridin-3-yl)methyl, (2-(cyano)pyridin-4-yl)methyl, (5-(cyano)pyridin-2-yl)methyl, (2-(chloro)pyridin-4-yl)methyl, pyrimidin-5-ylmethyl, 2-(pyrimidin-2-yl)propyl, thien-2-ylmethyl, and thien-3-ylmethyl.

The term "heteroarylalkylcarbonyl" as used herein, means a heteroarylalkyl, as defined herein, appended to the parent molecular moiety through a carbonyl group, as defined herein.

The term "heteroarylalkylthio" as used herein, means a heteroarylalkyl group, as defined herein, appended to the parent molecular moiety through a sulfur atom. Representative examples of heteroarylalkylthio include, but are not limited to, fur-3-ylmethylthio, 1H-imidazol-2-ylmethylthio, 1H-imidazol-4-ylmethylthio, pyridin-3-ylmethylthio, 6-chloropyridin-3-ylmethylthio, pyridin-4-ylmethylthio, (6-(trifluoromethyl)pyridin-3-yl)i-ethylthio, (6-(cyano)pyridin-3-yl)methylthio, (2-(cyano)pyridin-4-yl)methylthio, (5-(cyano)pyridin-2-yl)methylthio, (2-(chloro)pyridin-4-yl)methylthio, pyrimidin-5-ylmethylthio, 2-(pyrimidin-2-yl)propylthio, thien-2-ylmethylthio, and thien-3-ylmethylthio.

The term "heteroarylcarbonyl" as used herein, means a heteroaryl group, as defined herein, appended to the parent molecular moiety through a carbonyl group, as defined herein. Representative examples of heteroarylcarbonyl include, but are not limited to, fur-3-ylcarbonyl, 1H-imidazol-2-ylcarbonyl, 1H-imidazol-4-ylcarbonyl, pyridin-3-ylcarbonyl, 6-chloropyridin-3-ylcarbonyl, pyridin-4-ylcarbonyl, (6-(trifluoromethyl)pyridin-3-yl)carbonyl, (6-(cyano)pyridin-3-yl)carbonyl. (2-(cyano)pyridin-4-yl)carbonyl, (5-(cyano)pyridin-2-yl)carbonyl, (2-(chloro)pyridin-4-yl)carbonyl, pyrimidin-5-ylcarbonyl, pyrimidin-2-ylcarbonyl, thien-2-ylcarbonyl, and thien-3-ylcarbonyl.

The term "heteroaryloxy" as used herein, means a heteroaryl group, as defined herein, appended to the parent molecular moiety through an oxygen atom. Representative examples of heteroaryloxy include, but are not limited to fur-3-yloxy, 1H-imidazol-2-yloxy, 1H-imidazol-4-yloxy, pyridin-3-yloxy, 6-chloropyridin-3-yloxy, pyridin-4-yloxy, (6-(trifluoromethyl)pyridin-3-yl) oxy, (6-(cyano)pyridin-3-yl) oxy, (2-(cyano)pyridin-4-yl)oxy, (5-(cyano)pyridin-2-yl) oxy, (2-(chloro)pyridin-4-yl)oxy, pyrimidin-5-yloxy, pyrimidin-2-yloxy, thien-2-yloxy, and thien-3-yloxy.

The term "heteroaryloxyalkyl" as used herein, means a heteroaryloxy group, as defined herein, appended to the parent molecular moiety through an alkyl group, as defined herein. Representative examples of heteroaryloxyalkyl include, but are not limited to, pyridin-3-yloxymethyl and 2-quinolin-3-yloxyethyl.

The term "heteroarylthio" as used herein, means a heteroaryl group, as defined herein, appended to the parent molecular moiety through a sulfur atom. Representative examples of heteroarylthio include, but are not limited to, pyridin-3-ylthio and quinolin-3-ylthio.

The term "heteroarylthioalkyl" as used herein, means a heteroarylthio group, as defined herein, appended to the parent molecular moiety through an alkyl group, as defined herein. Representative examples of heteroarylthioalkyl include, but are not limited to, pyridin-3-ylthiomethyl, and 2-quinolin-3-ylthioethyl.

The term "heterocycle" or "heterocyclic" as used herein, means a monocyclic heterocycle, a bicyclic heterocycle or a tricyclic heterocycle. The monocyclic heterocycle is a 3, 4, 5, 6 or 7 membered ring containing at least one heteroatom independently selected from the group consisting of O, N, and S. The 3 or 4 membered ring contains 1 heteroatom selected from the group consisting of O, N and S. The 5 membered ring contains zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to azetidinyl, azepanyl, aziridinyl, diazepanyl. 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a 5 or 6 membered monocyclic heterocycle fused to a phenyl group, or a 5 or 6 membered monocyclic heterocycle fused to a cycloalkyl, or a 5 or 6 membered monocyclic heterocycle fused to a cycloalkenyl, or a 5 or 6 membered monocyclic heterocycle fused to a monocyclic heterocycle. The bicyclic heterocycle is connected to the parent molecular moiety through any carbon atom or any nitrogen atom contained within the bicyclic heterocycle. Representative examples of bicyclic heterocycle include, but are not limited to, 1,3-benzodioxolyl, 1,3-benzodithiolyl, 2,3-dihydro-1,4-benzodioxinyl, benzodioxolyl, 2,3-dihydro-1-benzofuranyl, 2,3-dihydro-1-benzothienyl, chromenyl and 1,2,3,4-tetrahydroquinolinyl. The tricyclic heterocycle is a bicyclic heterocycle fused to a phenyl, or a bicyclic heterocycle fused to a cycloalkyl, or a bicyclic heterocycle fused to a cycloalkenyl, or a bicyclic heterocycle fused to a monocyclic heterocycle. The tricyclic heterocycle is connected to the parent molecular moiety through any carbon atom or any nitrogen atom contained within the tricyclic heterocycle. Representative examples of tricyclic heterocycle include, but are not limited to, 2,3,4,4a,9,9a-hexahydro-1H-carbazolyl, 5a,6,7,8,9,9a-hexahydrodibenzo[b,d]furanyl, and 5a,6,7,8,9,9a-hexahydrodibenzo[b,d]thienyl.

The heterocycles of this invention are optionally substituted with 1, 2, 3 or 4 substituents independently selected from the group consisting of alkenyl, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, formyl, haloalkoxy, haloalkyl, halogen, hydroxy, hydroxyalkyl, mercapto, oxo, —$NZ_1Z_2$ and ($NZ_3Z_4$)carbonyl.

The term "heterocyclealkoxy" as used herein, means a heterocycle group, as defined herein, appended to the parent molecular moiety through an alkoxy group, as defined herein. Representative examples of heterocyclealkoxy include, but are not limited to, 2-pyridin-3-ylethoxy, 3-quinolin-3-ylpropoxy, and 5-pyridin-4-ylpentyloxy, The term "heterocyclealkyl" as used herein, means a heterocycle, as defined herein, appended to the parent molecular moiety through an alkyl group, as defined herein. Representative examples of heterocyclealkyl include, but are not limited to, The term "heterocyclealkylcarbonyl" as used herein, means a heterocyclealkyl, as defined herein, appended to the parent molecular moiety through a carbonyl group, as defined herein. Representative examples of heterocyclealkylcarbonyl include, but are not limited to, piperidin-4-ylmethylcarbonyl, piperazin-1-ylmethylcarbonyl, 3-methyl-1-pyrrolidin-1-yl-butylcarbonyl, (1R)-3-methyl-1-pyrrolidin-1-ylbutylcarbonyl, (1S)-3-methyl-1-pyrrolidin-1-ylbutylcarbonyl.

The term "heterocyclealkylthio" as used herein, means a heterocyclcalkyl group, as defined herein, appended to the parent molecular moiety through a sulfur atom. Representative examples of hieterocyclealkylthio include, but are not limited to, 2-pyridin-3-yletlhythio. 3-quinolin-3-ylpropylthio, and 5-pyridin-4-ylpentylthio.

The term "heterocyclecarbonyl" as used herein, means a heterocycle, as defined herein, appended to the parent molecular moiety through a carbonyl group, as defined herein.

The term "heterocyclecarbonylalkyl" as used herein, means a heterocyclecarbonyl, as defined herein, appended to the parent molecular moiety through an alkyl group, as defined herein.

The term "heterocycleoxy" as used herein, means a heterocycle group, as defined herein, appended to the parent molecular moiety through an oxygen atom. Representative examples of heterocycleoxy include, but are not limited to, pyridin-3-yloxy and quinolin-3-yloxy.

The term "heterocycleoxyalkyl" as used herein, means a heterocycleoxy group, as defined herein, appended to the parent molecular moiety through an alkyl group, as defined herein. Representative examples of heterocycleoxyalkyl include, but are not limited to, pyridin-3-yloxymethyl and 2-quinolin-3-yloxyethyl.

The term "heterocyclethio" as used herein, means a heterocycle group, as defined herein, appended to the parent molecular moiety through a sulfur atom. Representative examples of heterocyclethio include, but are not limited to, pyridin-3-ylthio and quinolin-3-ylthio.

The term "heterocyclethioalkyl" as used herein, means a heterocyclethio group, as defined herein, appended to the parent molecular moiety through an alkyl group, as defined herein. Representative examples of heterocyclethioalkyl include, but are not limited to, pyridin-3-ylthiomethyl, and 2-quinolin-3-ylthioethyl.

The term "hydroxy" as used herein, means an —OH group.

The term "hydroxyalkyl" as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "hydroxy-protecting group" or "O-protecting group" means a substituent which protects hydroxyl groups against undesirable reactions during synthetic procedures. Examples of hydroxy-protecting groups include, but are not limited to, substituted methyl ethers, for example, methoxymethyl, benzyloxymethyl, 2-methoxyethoxymethyl, 2-(trimethylsilyl)-ethoxymethyl benzyl, and triphenylmethyl; tetrahydropyranyl ethers; substituted ethyl ethers, for example, 2,2,2-trichloroethyl and t-butyl; silyl ethers, for example, trimethylsilyl, t-butyldimethylsilyl and t-butyldiphenylsilyl, cyclic acetals and ketals, for example, methylene acetal, acetonide and benzylidene acetal; cyclic ortho esters, for example, methoxymethylene; cyclic carbonates; and cyclic boronates. Commonly used hydroxy-protecting groups are disclosed in T. W. Greene and P. G. M. Wuts, *Protective Groups in Organic Synthesis,* 3rd edition, John Wiley & Sons, New York (1999).

The term "lower alkenyl" as used herein, is a subset of alkenyl, as defined herein, and means an alkenyl group containing from 2 to 4 carbon atoms. Examples of lower alkenyl are ethenyl, propenyl, and butenyl.

The term "lower alkoxy" as used herein, is a subset of alkoxy, as defined herein, and means a lower alkyl group, as defined herein, appended to the parent molecular moiety through an oxygen atom, as defined herein. Representative examples of lower alkoxy include, but are not limited to, methoxy, ethoxy, propoxy, 2-propoxy, butoxy, and tert-butoxy.

The term "lower alkyl" as used herein, is a subset of alkyl as defined herein and means a straight or branched chain hydrocarbon group containing from 1 to 4 carbon atoms. Examples of lower alkyl are methyl, ethyl, n-propyl, isopropyl, n-butyl, iso-butyl, sec-butyl, and tert-butyl.

The term "lower alkylthio" as used herein, is a subset of alkylthio, means a lower alkyl group, as defined herein, appended to the parent molecular moiety through a sulfur atom. Representative examples of lower alkylthio include, but are not limited, methylthio, ethylthio, and tert-butylthio.

The term "lower alkynyl" as used herein, is a subset of alkynyl, as defined herein, and means an alkynyl group containing from 2 to 4 carbon atoms. Examples of lower alkynyl are ethynyl, propynyl, and butynyl.

The term "lower haloalkoxy" as used herein, is a subset of haloalkoxy, as defined herein, and means a straight or branched chain haloalkoxy group containing from 1 to 4 carbon atoms. Representative examples of lower haloalkoxy include but are not limited to, trifluoromethoxy, trichloromethoxy, dichloromethoxy fluoromethoxy, and pentafluoroethoxy.

The term "lower haloalkyl" as used herein, is a subset of haloalkyl, as defined herein, and means a straight or branched chain haloalkyl group containing from 1 to 4 carbon atoms. Representative examples of lower haloalkyl include, but are not limited to, trifluoromethyl, trichloromethyl, dichloromethyl, fluoromethyl, and pentafluoroethyl.

The term "mercapto" as used herein, means a —SH group.

The term "mercaptoalkyl" as used herein, means a mercapto group, as defined herein, appended to the parent molecular moiety through an alkyl group, as defined herein. Representative examples of mercaptoalkyl include, but are not limited to, 2-mercaptoethyl and 3-mercaptopropyl.

The term "methylenedioxy" as used herein, means a —OCH$_2$O— group wherein the oxygen atoms of the methylenedioxy are attached to the parent molecular moiety through two adjacent carbon atoms.

The term "nitrogen protecting group" as used herein, means those groups intended to protect an amino group against undesirable reactions during synthetic procedures. Preferred nitrogen protecting groups are acetyl, benzoyl, benzyl, benzyloxycarbonyl (Cbz), formyl, phenylsulfonyl, tert-butoxycarbonyl (Boc), tert-butylacetyl trifluoroacetyl, and triphenylmethyl (trityl).

The term "nitro" as used herein, means a —NO$_2$ group.

The term "NZ$_1$Z$_2$" as used herein, means two groups, Z$_1$, and Z$_2$, which are appended to the parent molecular moiety through a nitrogen atom, Z$_1$, and Z$_2$ are each independently selected from the group consisting of hydrogen alkyl, alkylcarbonyl, alkoxycarbonyl, aryl, arylalkyl, formyl and (NZ$_5$Z$_6$)carbonyl. In certain instances within the invention, Z$_1$ and Z$_2$ taken together with the nitrogen atom to which they are attached form a heterocyclic ring. Representative examples of NZ$_1$Z$_2$ include, but are not limited to, amino, methylamino, acetylamino, acetylmethylamino, phenylamino, benzylamino, azetidinyl, pyrrolidinyl and piperidinyl.

The term "NZ$_3$Z$_4$" as used herein, means two groups, Z$_3$ and Z$_4$, which are appended to the parent molecular moiety through a nitrogen atom. Z$_3$ and Z$_4$ are each independently selected from the group consisting of hydrogen, alkyl, aryl and arylalkyl. Representative examples of $NZ_3Z_4$ include, but are not limited to amino, methylamino, phenylamino and benzylamino.

The term "$NZ_5Z_6$" as used herein, means two groups, $Z_5$ and $Z_6$, which are appended to the parent molecular moiety through a nitrogen atom. $Z_1$ and $Z_6$ are each independently selected from the group consisting of hydrogen, alkyl, aryl and arylalkyl. Representative examples of $NZ_5Z_6$ include, but are not limited to, amino, methylamino, phenylamino and benzylamino.

The term "$(NZ_3Z_4)$carbonyl" as used herein, means a $NZ_3Z_4$ group, as defined herein, appended to the parent molecular moiety through a carbonyl group, as defined herein. Representative examples of $(NZ_3Z_4)$carbonyl include, but are not limited to, aminocarbonyl, (methylamino)carbonyl, (dimethylamino)carbonyl, and (ethylmethylamino)carbonyl.

The term "oxo" as used herein, means a =O moiety.

The term "sulfinyl" as used herein, means a —S(O)— group.

The term "sulfonyl" as used herein, means a —SO$_2$— group.

The term "tautomer" as used herein means a proton shift from one atom of a compound to another atom of the same compound wherein two or more structurally distinct compounds are in equilibrium with each other.

Although typically it may be recognized that an asterisk is used to indicate that the exact subunit composition of a receptor is uncertain, for example α3b4* indicates a receptor that contains the β3 and α4 proteins in combination with other subunits, the term α7 as used herein is intended to include receptors wherein the exact subunit composition is both certain and uncertain. For example, as used herein α7 includes homomeric α7)$_5$ receptors and α7* receptors, which denote a nAChR containing at least one α7 subunit.

Compounds of the Invention

Compounds of the invention can have the formula (I) as described in the Summary of the Invention Within the scope of the invention, the compounds of the invention have the formula (II), (III), (IV)

(II)

(III)

(IV)

wherein $L^1$, $L^2R^{x1}$, $R^{x2}$, $R^{x3}$, and $R^{x4}$ are each independently defined in formula (I).

In one embodiment, the compounds of the invention can have the formula (II), (III) or (IV), wherein $L^2$, $R^{x1}$, $R^{x2}$, $R^{x3}$, and $R^{x4}$ are as described in formula (I); $L^1$ is selected from O and $NR^b$.

In another embodiment compounds of the invention can have the formula (II), (III) or (IV), wherein $R^{x1}$, $R^{x2}$, $R^{x3}$, and $R^{x4}$ are as described in formula (I). $L^1$ is selected from O and $NR^b$. $L^2$ is selected from $CH_2$, O, and $NR^b$.

In one more embodiment, compounds of the invention can have the formula (II), (III) or (IV), wherein $L^1$ is selected from O and $NR^b$. $L^2$ is selected from $CH_2$, O, $NR^b$, $R^{x1}$, $R^{x2}$, $R^{x3}$, and $R^{x4}$ are particularly selected from H, alkyl, aryl, halogen, heteroaryl, $OR^b$, and $NR^dR^e$, and more particularly selected from aryl and heteroaryl groups having the structures (V)

(VI)

and (VII)

wherein
$X^5$ is $CR^{x5}$ or N;
$X^6$ is $CR^{x6}$ or N;
$X^7$ is $CR^{x7}$ or N;
$X^8$ is $CR^{x8}$ or N;
$X^9$ is $CR^{x9}$ or N;
$X^{10}$ is $CR^{x10}$ or N;
$Y_1$ is $CR^{y1}$, N; O, or S;
$Y_2$ is $CR^{y2}$, N; O, or S;
$Y_3$ is $CR^{y3}$, N; O, or S;
$Y_4$ is $CR^{y4}$, N; O, or S;
$Y_5$ is $CR^{y5}$, N; O, or S;
$R^{x5}$, $R^{x6}$, $R^{x7}$, $R^{x8}$, $R^{x9}$ and $R^{x10}$ are each independently H, alkyl, aryl, cycloalkyl, halogen, halo alkyl, heteroaryl, $OR^b$, $NR^dR^e$, $COR^b$, CN, $CO_2R^b$, or $CONR^dR^e$;

$R^{y1}$, $R^{y2}$, $R^{y3}$ and $R^{y4}$ are each independently H, alkyl, aryl, cycloalkyl, halogen, halo alkyl, heteroaryl, $OR^b$, $NR^dR^c$, $COR^b$, CN, $CO_2R^b$, or $CONR^dR^e$; and $R^{y5}$ is H, alkyl, aryl, alkylcarbonyl, alkoxylcarbonyl, or heteroaryl.

Examples of specific aryl and heteroaryl groups suitable for compounds of formula (V), (VI), and (VII) include, but are not limited to, imidazolyl, isoimidazolyl, isoxazolyl, isothiazolyl, furyl, oxazolyl, phenyl, pyridinyl, pyrimidinyl, pyridazinyl, pyrazinyl, thiophenyl, 1,3-thiazolyl, 1,3,4-thiadiazolyl, 1,3,4-oxadiazolyl, benzofuranyl, benzo[d]imidazolyl, benzo[d]isoxazolyl, benzo[d]isothiazolyl, benzo[d]oxazolyl, benzo[d]thiazolyl, benzo[b]thiophenyl, furo[3,2-b]pyridinyl, furo[3,2-c]pyridinyl, imidazo[4,5-b]pyridinyl, imidazo[4,5-c]pyridine, indolyl, indazolyl, isoxazolo[4,5-b]pyridinyl, isoxazolo[4,5-c]pyridinyl, isoxazolo[5,4-b]pyridinyl, isoxazolo[5,4-c]pyridinyl, isothiazolo[4,5-c]pyridinyl, isothiazolo[4,5-c]pyridinyl, isothiazolo[5,4-b]pyridinyl, isothiazolo[5,4-c]pyridinyl, oxazolo[4,5-b]pyridinyl, oxazolo[4,5-c]pyridinyl, oxazolo[5,4-b]pyridinyl, oxazolo[5,4-c]pyridinyl, pyrazolo[3,4-b]pyridinyl, pyrazolo[3,4-c]pyridinyl, pyrazolo[4,3-b]pyridinyl, pyrazolo[4,3-c]pyridinyl, pyrrolo[2,3-b]pyridinyl, pyrrolo[2,3-c]pyridinyl, pyrrolo[3,2-b]pyridinyl, pyrrolo[3,2-c]pyridinyl, thiazolo[4,5-b]pyridinyl, thiazolo[4,5-c]pyridinyl, thiazolo[5,4-b]pyridinyl, thiazolo[5,4-c]pyridinyl, thieno[2,3-b]pyridinyl, thieno[2,3-c]pyridinyl, thieno[3,2-b]pyridinyl, and thieno[3,2-c]pyridinyl. Preferred aryl and heteroaryl groups are indolyl, phenyl, pyridinyl, pyrazolyl, and pyrrolopyridinyl. The individual corresponding aryl and heteroaryl groups can be optionally substituted with 0, 1, 2, 3, 4 or 5 substituents selected from H, alkyl, aryl, cyclic alkyl, halogen, halo alkyl, heteroaryl, $OR^b$, $NR^dR^e$, $COR^b$, CN, $CO_2R^b$, and $CONR^dR^e$.

Specific embodiments contemplated as part of the invention include, but are not limited to compounds of formula (I), salts, or prodrugs thereof, for example:

3H-(4's)-1'-azaspiro[benzofuran-2,4']-tricyclo[3.3.1.1$^{3,7}$]decane;

3H-(4's)-1'-azaspiro[5-bromobenzofuran-2,4']-tricyclo[3.3.1.1$^{3,7}$]decane;

3H-(4's)-1'-azaspiro[5-phenylbenzofuran-2,4']-tricyclo[3.3.1.1$^{3,7}$]decane;

3H-(4's)-1'-azaspiro[5-(indol-5-yl)-benzofuran-2,4']-tricyclo[3.3.1.1$^{3,7}$]decane;

3H-(4's)-1'-azaspiro[5-(indol-6-yl)-benzofuran-2,4']-tricyclo[3.3.1.1$^{3,7}$]decane;

3H-(4's)-1'-azaspiro[5-(indol-4-yl)-benzofuran-2,4']-tricyclo[3.3.1.1$^{3,7}$]decane;

3H-(4'r)-1'-azaspiro[benzofuran-2,4']-tricyclo[3.3.1.1$^{3,7}$]decane;

3H-(4'r)-1'-azaspiro[5-bromobenzofuran-2,4']-tricyclo[3.3.1.1$^{3,7}$]decane;

3H-(4'r)-1'-azaspiro[5-phenylbenyofuran-2,4']-tricyclo[3.3.1.1$^{3,7}$]decane;

3H-(4'r)-1'-azaspiro[5-(indol-5-yl)-benzofuran-2,4']-tricyclo[3.3.1.1$^{3,7}$]decane;

3H-(4'r)-1'-azaspiro[5-(benzo[b]thiophen-5-yl)-benzofuran-2,4']-tricyclo[3.3.1.1$^{3,7}$]decane;

3H-(4'r)-1'-azaspiro[5-(indol-4-yl)-benzofuran-2,4']-tricyclo[3.3.1.1$^{3,7}$]decane;

3H-(4'r)-1'-azaspiro[5-(2-oxo-indolin-5-yl)-benzofuran-2,4']-tricyclo[3.3.1.1$^{3,7}$]decane;

3H-(4'r)-1'-azaspiro[5-(thiophen-3-yl)-benzofuran-2,4']-tricyclo[3.3.1.1$^{3,7}$]decane;

3H-(4'r)-1'-azaspiro[5-(1H-pyrrolo[2,3-b]pyridin-5-yl)-benzofuran-2,4']-tricyclo[3.3.1.1$^{3,7}$]decane; and 3H-(4'r)-1'-azaspiro[5-(thieno[2,3-b]pyridin-5-yl)-benzofuran-2,4']-tricyclo[3.3.1.1$^{3,7}$]decane.

Compounds of the invention may exist as stereoisomers wherein, asymmetric or chiral centers are present. These stereoisomers are "R" or "S" depending on the configuration of substituents around the chiral element. The terms "R" and "S" used herein are configurations as defined in IUPAC 1974 Recommendations for Section E, Fundamental Stereochemistry, Pure Appl. Chem., 1976, 45: 13-30. The invention contemplates various stereoisomers and mixtures thereof and are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomels by recrystallization or chromatography and optional liberation of the optically pure product from the auxiliary as described in Furniss, Hannaford, Smith and Tatchell, "Vogel's Textbook of Practical Organic Chemistry". 5th edition (1989). Longman Scientific & Technical. Essex CM20 2JE, England, or (2) direct separation of the mixture of optical enantiomers on chiral chromatographic columns or (3) fractional recrystallization methods.

More particularly, the compounds of the invention can exist in the forms represented by formulas

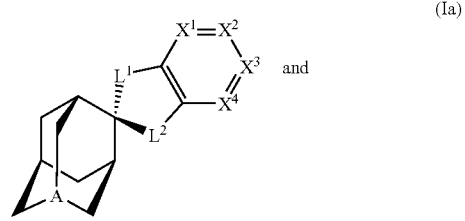

(Ia)

and

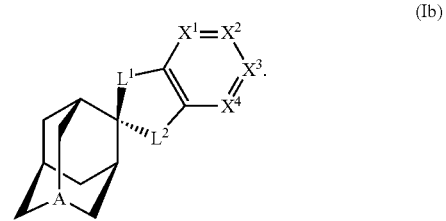

(Ib)

The aza-adamantane portion of isomer (Ia) and isomer (Ib) is not chiral, however the C4 carbon at which $L_1$ is attached is considered pseudoasymmetric. Compounds represented by formula (Ia) and (Ib) are diastereomers. The configurational assignment of structures of formula (Ia) are assigned 4s in accordance with that described in Synthesis. 1992, 1080. Becker, D. P.; Flynn. D. L. and as defined in Stereochemistry of Organic Compounds. E. L. Eliel. S. H Wilen; John Wiley and Sons, Inc. 1994. In addition the configurational assignment of structures of formula (Ib) are assigned 4r using the same methods.

The isomers (Ia) and (Ib) may be synthesized separately using the individual stereoisomers according to the Schemes or the Experimentals described herein. Alternatively, isomers (Ia) and (Ib) may be synthesized together after which the individual isomers may be separated by chromatographic methods from the mixture of both isomers when mixtures of stereoisomers are used in the synthesis.

It is contemplated that a mixture of both isomers may be used to modulate the effects of nAChRs. Furthermore, it is contemplated that the individual isomers of formula (Ia) and (Ib) may be used alone to modulate the effects of nAChRs. Therefore, it is contemplated that either a mixture of the compounds of formula (Ia) and (Ib) or the individual isomers alone represented by the compounds of formula (Ia) or (Ib) would be effective in modulating the effects of nAChRs, and more particularly α7 nAChRs and is thus within the scope of the invention.

Methods of the Invention

Compounds and compositions of the invention are useful for modulating the effects of nAChRs, and more particularly α7 nAChRs. In particular, the compounds and compositions of the invention can be used for treating or preventing disorders modulated by α7 nAChRs. Typically, such disorders can be ameliorated by selectively modulating the α7 nAChRs in a mammal, preferably by administering a compound or composition of the invention, either alone or in combination with another active agent, for example, as part of a therapeutic regimen.

In addition, the invention relates to a method for treating or preventing conditions, disorders or deficits modulated by an α7 nicotinic acetylcholine receptor, an α4β2 nicotinic acetylcholine receptor or both α7 and α4β2 nicotinic acetylcholine receptors wherein the condition, disorder, or deficit is selected from the group consisting of a memory disorder, cognitive disorder, neurodegeneration, or neurodevelopmental disorder, or a combination thereof, comprising administration of a therapeutically suitable amount of a compound of formula (I),

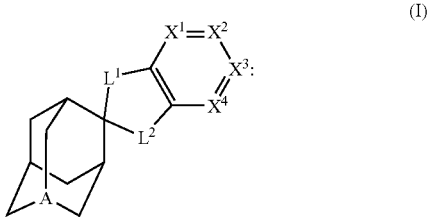

(I)

or a pharmaceutically acceptable salt or prodrug thereof, wherein A, $L^1$, $L^2$, $X^1$, $X^2$, $X^3$, and $X^4$ are as previously defined.

The invention also contemplates the method for treating or preventing a condition or disorder modulated by an α7 nicotinic acetylcholine receptor comprising the step of administering a compound of the formula (I), wherein the condition or disorder is selected from a memory disorder, cognitive disorder, neurodegeneration, and neurodevelopmental disorder.

The invention also contemplates a method for treating or preventing a condition or disorder modulated by an α7 nicotinic acetylcholine receptor comprising the step of administering a compound of the formula (I), wherein the condition or disorder is selected from attention deficit disorder, attention deficit hyperactivity disorder (ADHD), Alzheimer's disease (AD), mild cognitive impairment, schizophrenia, senile dementia, AIDS dementia, Pick's Disease, dementia associated with Lewy bodies, dementia associated with Down's syndrome, amyotrophic lateral sclerosis, Huntington's disease, diminished CNS function associated with traumatic brain injury, acute pain, post-surgical pain, chronic pain, and inflammatory pain.

The invention also contemplates a method for treating or preventing a condition or disorder modulated by an α7 nicotinic acetylcholine receptor comprising the step of administering a compound of the formula (I), wherein the condition or disorder is schizophrenia.

The invention also contemplates a method for treating or preventing a condition or disorder modulated by an α7 nicotinic acetylcholine receptor comprising the step of administering a compound of the formula (I) in combination with an atypical antipsychotic.

The invention also contemplates a method for treating or preventing a condition or disorder modulated by an α7 nicotinic acetylcholine receptor comprising the step of administering a compound of the formula (I), wherein the condition or disorder is infertility, lack of circulation, need for new blood vessel growth associated with wound healing, more particularly circulation around a vascular occlusion, need for new blood vessel growth associated with vascularization of skin grafts, ischemia, inflammation, particularly those associated with rheumatoid arthritis, wound healing, and other complications associated with diabetes.

The invention also contemplates a method for treating or preventing a condition or disorder modulated both by α7 and α4β2 nicotinic acetylcholine receptor comprising the step of administering a compound of the formula (I), wherein the condition or disorder is selected from a group of disorders where both α7 and α4β2 nicotinic receptors are implicated. These include attention deficit disorder, attention deficit hyperactivity disorder (ADHD), Alzheimer's disease (AD), mild cognitive impairment, schizophrenia, senile dementia, AIDS dementia, Pick's Disease, dementia associated with Lewy bodies, dementia associated with Down's syndrome, amyotrophic lateral sclerosis, Huntington's disease, inflammation, arthritis of various types, smoking cessation, traumatic brain injury, acute pain, post-surgical pain, osteoarthritic pain, neuropathic, and inflammatory chronic pain states.

Compounds for the method of the invention, including but not limited to those specified in the examples or otherwise specifically named, can modulate, and often possess an affinity for, nAChRs, and more particularly α7 nAChRs. As α7 nAChRs ligands, the compounds of the invention can be useful for the treatment or prevention of a number of α7 nAChR-mediated diseases or conditions. Certain compounds of the invention demonstrate, in addition to affinity for α7 nAChRs, affinity for α4β2 nAChRs.

For example, α7 nAChRs have been shown to play a significant role in enhancing cognitive function, including aspects of learning, memory, and attention (Levin, E. D., J. Neurobiol. 53: 633-640, 2002). As such, α7 ligands are suitable for the treatment of conditions and disorders related to memory, cognition, or both including, for example, attention deficit disorder, attention deficit hyperactivity disorder (ADHD), Alzheimer's disease (AD), mild cognitive impairment, senile dementia, AIDS dementia, Pick's Disease, dementia associated with Lewy bodies, and dementia associated with Down's syndrome, as well as cognitive deficits associated with schizophrenia.

In addition, α7-containing nAChRs have been shown to be involved in the cytoprotective effects of nicotine both in vitro (Jonnala, R. B. and Buccafusco, J. J., J. Neurosci. Res. 66: 565-572, 2001) and in vivo (Shimohama, S. et al., Brain Res. 779: 359-363, 1998). More particularly, neurodegeneration underlies several progressive CNS disorders, including, but not limited to, Alzheimer's disease, Parkinson's disease, amyotrophic lateral sclerosis, Huntington's disease, dementia with Lewy bodies, as well as diminished CNS function resulting from traumatic brain injury. For example, the impaired function of α7 nAChRs by β-amyloid peptides linked to Alzheimer's disease has been implicated as a key factor in development of the cognitive deficits associated with the disease (Liu, Q.-S., Kawai, H., Berg, D. K., PNAS 98: 4734-4739, 2001). α7 selective ligands can influence neuroprotective pathways leading to decreased phosphorylation of the tau protein, whose hyperphosphorylation is required for neurofibrillary tangle formation in various tau related pathologies such as Alzheimer's disease and various other dementias (Bitner et al., Soc Neuroscience, 2006 abst 325.6). The activation of α7 nAChRs has been shown to block this neurotoxicity (Kihara, T. et al., J. Biol. Chem. 276: 13541-13546, 2001). As such, selective ligands that enhance α7 activity can counter the deficits of Alzheimer's and other neurodegenerative diseases.

Alpha-7 nAChRs also have been implicated in aspects of neurodevelopment, for example neurogenesis of the brain. (Falk, L. et al., Developmental Brain Research 142:151-160, 2003; Tsuneki, H., et al., J. Physiol. (London) 547:169-179, 2003; Adams, C. E., et al., Developmental Brain Research 139:175-187, 2002). As such, α7 nAChRs can be useful in preventing or treating conditions or disorders associated with impaired neurodevelopment, for example schizophrenia. (Sawa A., Mol. Med. 9:3-9, 2003).

Several compounds with high affinity for α4β2 NNRs have been shown to improve attentive and cognitive performance in preclinical models that are relevant to attention-deficit/hyperactivity disorder (ADHD), a disease characterized by core symptoms of hyperactivity, inattentiveness, and impulsivity. For example, ABT-418, a full agonist at α4β2 NNRs, is efficacious in a variety of preclinical cognition models. ABT-418 administered transdermally, was shown in a controlled clinical trial in 32 adults to be effective in treating ADHD in general, and attention/cognitive deficits in particular (Wilens et al 1999). Likewise, ABT-418 showed a signal of efficacy in a pilot Alzheimer's disease trial. ABT-089, a α4β2 selective partial agonist, has been shown in rodent and primate animal models to improve attention, learning, and memory deficits. ABT-089 and another α4β2 agonist, ispronicline, has shown efficacy in a pilot clinical trials. In addition to cognition, compounds that interact with α4β2 nAChRs such as ABT-594 and others are also efficacious in preclinical and clinical models of pain. As such, ligands that modulate both α7 and α4β2 activity can have broader spectrum of therapeutic efficacy in disease states such as those involving cognitive deficits, attentive deficits, pain, neurodegenerative diseases, and others.

Schizophrenia is a complex disease that is characterized by abnormalities in perception, cognition, and emotions. Significant evidence implicates the involvement of α7 nAChRs in this disease, including a measured deficit of these receptors in post-mortem patients (Sawa A. Mol. Med. 9:3-9, 2003; Leonard, S. Eur. J. Pharmacol. 393: 237-242, 2000). Deficits in sensory processing (gating) are one of the hallmarks of schizophrenia. These deficits can be normalized by nicotinic ligands that operate at the α7 nAChR (Adler L. E. et al., Schizophrenia Bull. 24: 189-202, 1998; Stevens, K. E. et al., Psychopharmacology 136: 320-327, 1998). More recent studies have shown that α4β2 nicotinic receptor stimulation also contributes to the effects of nicotine in the DBA/2 mouse model of sensory gating (Radek et al., Psychopharmacology (Berl), 2006 187:47-55. Thus α7 and α7/α4β2 ligands demonstrate potential in the treatment schizophrenia.

Angiogenesis, a process involved in the growth of new blood vessels, is important in beneficial systemic functions, such as wound healing, vascularization of skin grafts, and enhancement of circulation, for example, increased circulation around a vascular occlusion. Non-selective nAChR agonists like nicotine have been shown to stimulate angiogenesis (Heeschen. C. et al., Nature Medicine 7: 833-839, 2001). Improved angiogenesis has been shown to involve activation of the α7 nAChR (Heeschen, C. et al. J. Clin. Invest. 110: 527-536, 2002). For example, improved conditions related to inflammation, ischemia, cardiac ischemia, and wound healing, for example in diabetic persons, have been associated with α7 nAChR activity (Jacobi, J., et al., Am. J. Pathol. 161:97-104, 2002). Therefore, nAChR ligands that are selective for the α7 subtype offer improved potential for stimulating angiogenesis with an improved side effect profile.

A population of α7 or α4β2 nAChRs in the spinal cord modulate neurotransmission transmission that have been associated with the pain-relieving effects of nicotinic compounds (Cordero-Erausquin, M. and Changeux, J.-P. PNAS 98:2803-2807, 2001). The α7 nAChR and α7/α4β2 ligands demonstrate therapeutic potential for the treatment of pain states, including acute pain post-surgical pain, as well as chronic pain states including inflammatory pain and neuropathic pain. Moreover, α7 nAChRs are expressed on the surface of primary macrophages that are involved in the inflammation response, and that activation of the α7 receptor inhibits release of TNF and other cytokines that trigger the inflammation response (Wang. H. et al Nature 421: 384-388, 2003). Therefore, selective α7 ligands demonstrate potential for treating conditions involving inflammation including those associated with various forms of arthritis.

The mammalian sperm acrosome reaction is an exocytosis process important in fertilization of the ovum by sperm. Activation of an α7 nAChR on the sperm cell has been shown to be essential for the acrosome reaction (Son, J. H. and Meizel, S. Biol. Reproduct. 68: 1348-1353 2003). Consequently, selective α7 agents demonstrate utility for treating fertility disorders.

Compounds of the invention are particularly useful for treating and preventing a condition or disorder affecting memory, cognition, neurodegeneration, neurodevelopment, and schizophrenia.

Cognitive impairment associated with schizophrenia often limits the ability of patients to function normally, a symptom not adequately treated by commonly available treatments, for example, treatment with an atypical antipsychotic. (Rowley, M. et al., J. Med. Chem. 44: 477-501, 2001). Such cognitive deficit has been linked to dysfunction of the nicotinic cholinergic system in particular with decreased activity at α7 receptors. (Friedman, J. I. et al. Biol Psychiatry, 51: 349-357, 2002). Thus, activators of α7 receptors can provide useful treatment for enhancing cognitive function in schizophrenic patients who are being treated with atypical antipsychotics. Accordingly, the combination of an α7 nAChR ligand and an atypical antipsychotic would offer improved therapeutic utility. Specific examples of suitable atypical antipsychotics include, but are not limited to, clozapine, risperidone, olanzapine, quietapine, ziprasidone, zotepine, iloperidone, and the like.

Actual dosage levels of active ingredients in the pharmaceutical compositions of this invention can be varied so as to obtain an amount of the active compound(s) that is effective to achieve the desired therapeutic response for a particular patient considering the composition and the method of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salt, ester, amide, or prodrug form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder: activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal range from about 0.10 μg/kg body w eight to about 10 mg/kg body weight. More preferable doses can be in the range of from about 0.10 μg/kg body weight to about 1 mg/kg body weight. If desired, the effective daily dose can be divided into multiple doses for purposes of administration. Consequently, single dose compositions may contain such amounts or submultiples thereof to make up the daily dose.

Methods for Preparing Compounds of the Invention

As used in the descriptions of the schemes and the examples, certain abbreviations are intended to have the following meanings: Bu for butyl; DMAP for 4-dimethylaminopyridine; DMF for dimethyl formamide: DME for 1,2-dimethoxyethane; Et for ethyl; EtOAc for ethyl acetate; HPLC for high pressure liquid chromatography; Me for methyl; MeOH for methanol; OAc for acetoxy; Pd/C for palladium on carbon; Ph for phenyl; and THF for tetrahydrofuran.

The reactions exemplified in the schemes are performed in a solvent appropriate to the reagents and materials employed and suitable for the transformations being effected. The described transformations may require modifying the order of the synthetic steps or selecting one particular process scheme over another in order to obtain a desired compound of the invention, depending on the functionality present on the molecule.

Nitrogen protecting groups can be used for protecting amine groups present in the described compounds. Such methods, and some suitable nitrogen protecting groups, are described in Greene and Wuts (Protective Groups In Organic Synthesis. Wiley and Sons, 1999). For example, suitable nitrogen protecting groups include, but are not limited to tert-butoxycarbonyl (Boc), benzyloxycarbonyl (Cbz), benzyl (Bn), acetyl, and trifluoroacetyl. More particularly, the BOC protecting group may be removed by treatment with an acid such as trifluoroacetic acid or hydrochloric acid. The Cbz and Bn protecting groups may be removed by catalytic hydrogenation. The acetyl and trifluoroacetyl protecting groups may be removed by a hydroxide ion.

Scheme 1

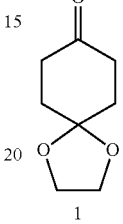

TOSMIC
KOtBu, DME

LiAlH₄
THF

(HCHO)ₙ
H₂SO₄, EtOH

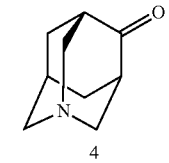

As outlined in Scheme 1, compound of formula 1 (commercially available from Aldrich Chemical Co., [4746-97-8]) when treated with tosylmethyl isocyanide (TOSMIC, commercially available from Aldrich Chemical Co., [36635-61-7]) in the presence of a base such as potassium tert-butoxide in a solvent such as ethylene glycol dimethyl ether will provide the compound of formula 2. Compound of formula 2 when treated with lithium aluminum hydride in THF will provide the compound of formula 3. Compound of formula 3 when treated with paraformaldehyde along with sulfuric acid in ethanol will provide the compound of formula 4 (1-azaadamantan-4-one). A further description of the synthesis may be found in Synthesis, 1992, 1080, Becker. D. P.; Flynn, D. L.

Scheme 2

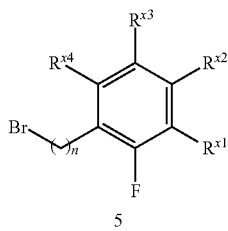

5

Mg, or EtMgBr, or PhLi

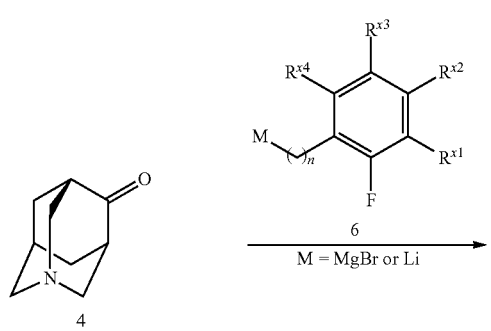

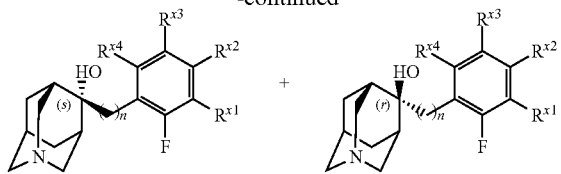

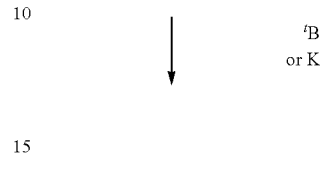

'BuOK
or KHMDS

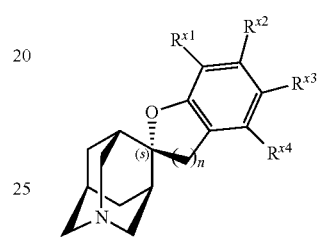
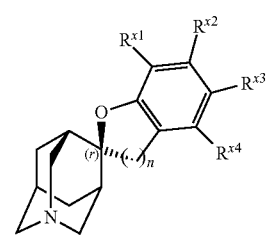

As outlined in Scheme 2, compounds of formula 5, wherein $R^{x1}$, $R^{x2}$, $R^{x3}$, and $R^{x4}$ are defined in formula (I), and n is selected from 1, 2, and 3, when treated with a metal, such as, but not limited to, lithium or magnesium, or an organic metal reagent, such as, but not limited to, EtMgBr or 'BuLi, will provide compound of formula 6, wherein M is MgBr or Li. Compounds of formula 6 when treated with azaadmantanone (4) in an organic solvent, such as but not limited to Et$_2$O THF, or DME, will provide compounds of formula 7 and 8. (r) and (s) isomers respectively, which may be seperated through chromatographic methods as known to one skilled in the art. The individual isomers or the mixture of both compounds of formular 7 and compounds of formula 8 when further treated with a base, such as 'BuOK or KHMDS, will provide a spiro ether of formula 9 and 10, respectively. When a mixture of compounds of formula 7 and of formula 8 are used, the individual, (s)-isomer of formula 9 and or (r) isomer of formular 10 may be separated through chromatographic methods that are known to one skilled in the art.

Scheme 3

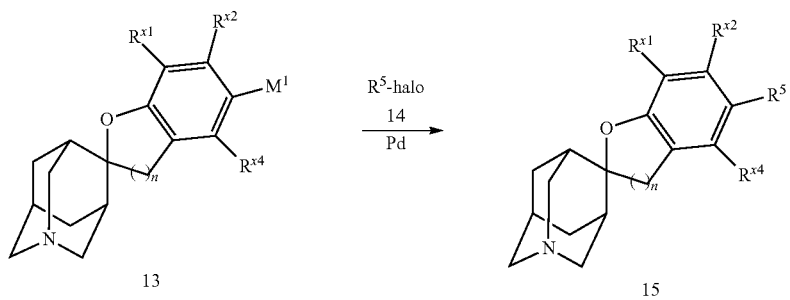

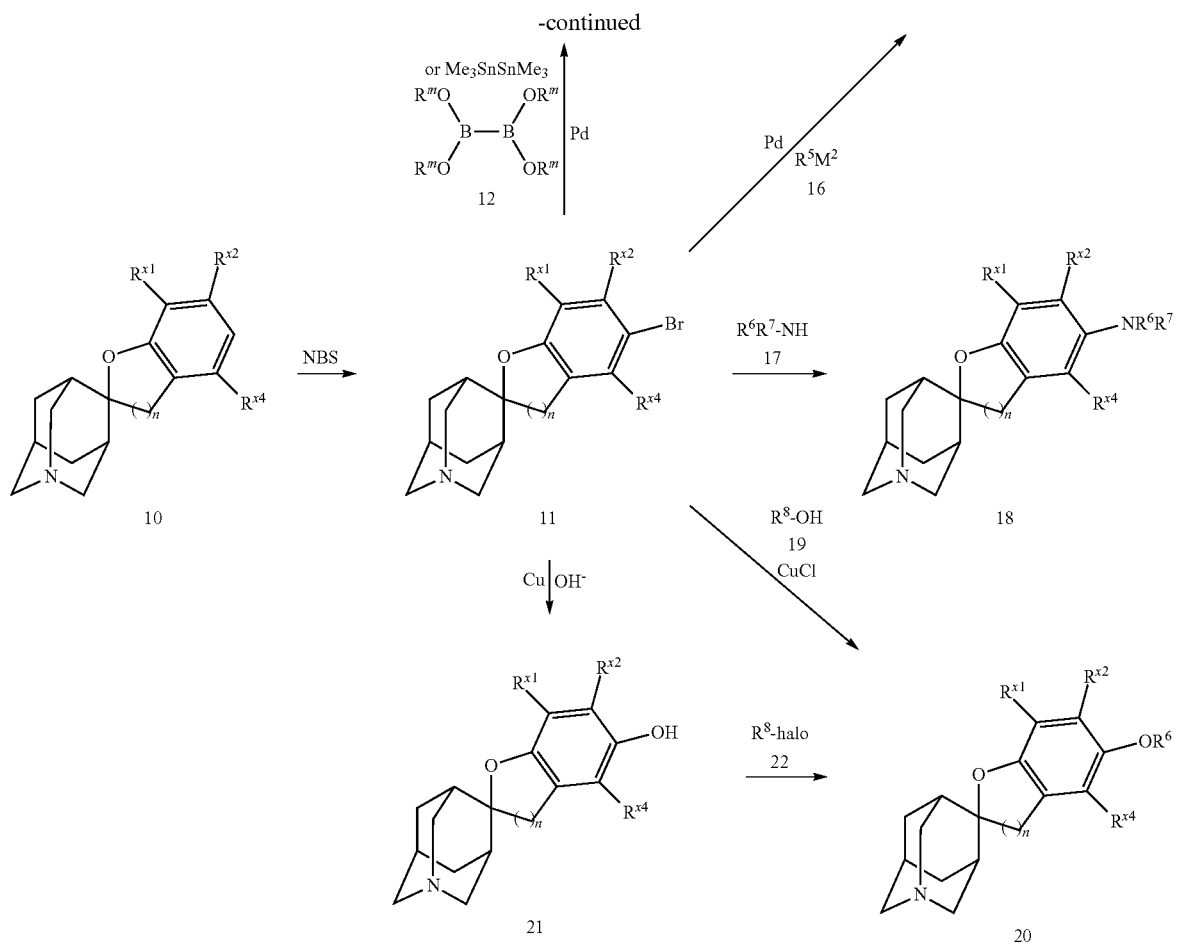

As outlined in Scheme 3, compounds of formula 10, which may be either the mixture or the individual isomers represented by the compounds of formula 8 and 9, wherein n, $R^{x1}$, $R^{x2}$, and $R^{x4}$ are as defined in formula (I), when treated with N-bromosuccinimide in presence an acid, such as, but not limited to, acetic acid, in a solvent, for example acetonitrile, will provide compounds of formula (I). Compounds of formula 11 when treated with a hexamethylditin or an organoboron compound of formula 12, such as bis(pinacolato)diboron or bis(catecholato)diboron, wherein $R^m$ is hydrogen, alkyl, or aryl, in the presence of a palladium catalyst, such as, but not limited to, $PdCl_2(PPh_3)_2$ or $PdCl_2(dppf)$, will provide the corresponding tin or boronic acid/esters of formula 13, wherein $M^1$ is —$SnMe_3$ or —$B(OR^m)_2$. Compounds of formula 13 when treated with compounds of formula 14 wherein $R^5$ is an aryl or heteroaryl ring and halo is bromide, chloride, or iodide, in the presence of a palladium catalyst, such as, but not limited to, $Pd(OAc)_2$, $PdCl_2(PPh_3)_2$, $Pd(PPh_3)_4$, $PdCl_2(dppf)$, or $Pd_2(dba)_3$, will provide compounds of formula 15. Alternatively, compounds of formula 11 when treated with compound of formula 16, wherein $R^5$ is an aryl or heteroaryl ring and $M^2$ is —$SnMe_3$ or —$B(OR^m)_2$, which is either commercially available, or prepared from compound of formula 14 by methods well-known to those skilled in the art, in the presence of a palladium catalyst, such as, but not limited to, $Pd(OAc)_2$, $PdCl_2(PPh_3)_2$, $Pd(PPh_3)_4$, $PdCl_2(dppf)$ or $Pd_2(dba)_3$, will provide compounds of formula 15. Compounds of formula 11 when treated with compounds of formula 17, wherein $R^6$ and $R^7$ are each independently H, alkyl, aryl, alkoxycarbonyl, arylcarbonyl, cyclicalkyl, or heteroaryl, in the presence of a ligand, such as, but not limited to, BINAP, Xantphos, dicyclohexyl(2',4',6'-triisopropylbiphenyl-2-yl) phosphine, dicyclohexyl(2',6'-diisopropoxybiphenyl-2-yl) phosphine, or 2'-(dicyclohexylphosphino)-N,N-dimethylbiphenyl-2-amine, and a palladium catalyst, such as, but not limited to, $Pd(OAc)_2$, $PdCl_2(PPh_3)_2$, $Pd(PPh_3)_4$, $PdCl_2$ (dppf), or $Pd_2(dba)_3$, with a base, for example $^tBuONa$ or $Cs_2CO_3$, in a solvent, such as, but not limited to, toluene at 110° C. as described in Org. Lett., 2005, 7, 3965, will provide compounds of formula 18. Compound of formula 11 when treated with an alcohol of formula 19, wherein $R^8$ is alkyl, in presence of a base, such as, but not limited to, NaH or $^tBuOK$, in an organic solvent such as, but not limited to, DMF or THF, will provide compound of formula 20. Alternatively, when compounds of formula 11 treated with compound of formula 19, wherein $R^8$ is an aryl group, in the presence of a copper catalyst, such as, but not limited to, Cu, CuCl, or CuI, and a ligand, such as, but not limited to, 2,2,6,6-tetramethylheptane-3,5-dione, and $Cs_2CO_3$ will provide compounds of formula 20 as described in Org. Lett. 2002, 4, 1623. Compound of formula 11 when treated with an aqueous basic solution, such as, but not limited to, NaOH or KOH, in the presence of a copper catalyst, such as, but not limited to, copper, CuCl or CuI, and an amino acid additive, such as, but not limited to, L-pyrroline, at high temperature using microwave heating will provide a compound of formula 21. Compounds of formula 21 when treated with alkyl halide of formula 22, wherein $R^8$ is alkyl, and halo is chloro, bromo or iodo, in the presence of a base, such as, but not limited to, $Na_2CO_3$, NaH, or NaHMDS, will provide compounds of formula 20. On the other hand, compounds of formula 21 when treated with an aryl halide of formula 22, wherein $R^9$ is aryl, and halo is chloro, bromo, or iodo, in the presence of a copper catalyst, such as, but not limited to, Cu, CuCl, or CuI, a ligand, such as, but not limited to, 2,2,6,6-tetramethylheptane-3,5-dione, and $Cs_2CO_3$ will provide compound of formula 20.

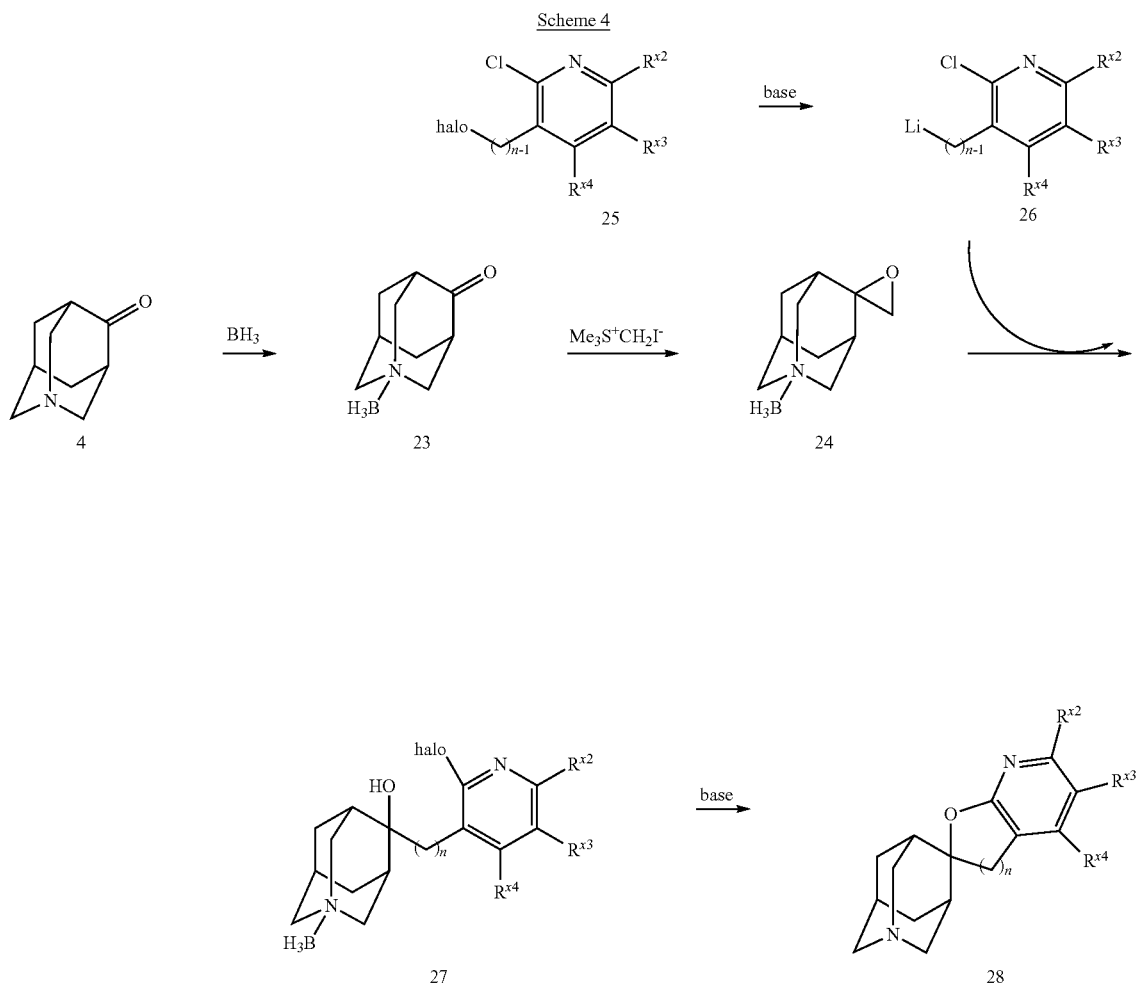

As shown in Scheme 4, compound of formula 4 when treated with borane-THF complex in THF will provide the borane complexed amine of formula 23, which when further treated with trimethylsulfoxonium iodide in the presence of, but not limited to, NaH will provide (rs) mixture of oxirane of formula 24. Compounds of formula 25, wherein n, $R^{x2}$, $R^{x3}$, and $R^{x4}$ are previously defined and halo is bromo or iodo, when treated with tert-butyl lithium or phenyl lithium, will provide compound of formula 26, which when further treated with the compound of formula 24 will provide a (rs) mixture of compounds of formula 27. The (rs) mixture of compounds of formula 27, when treated with a base, such as, but not limited to, $^tBuOK$ or KLMDS, will provide either (rs) mixture of the spiro ether containing compounds of formula 28, which may be separated using chromatographic methods known to one skilled in the art. Alternatively, the (rs) mixture of compounds of formula 27 may be separated using chromatographic methods to obtain the individual (r) or (s) isomers which, when treated individually with a base such as, but not limited to, $^tBuOK$ or KHMDS, will provide either the individual (r) or (s) isomer of the spiro ether containing compounds of formula 28.

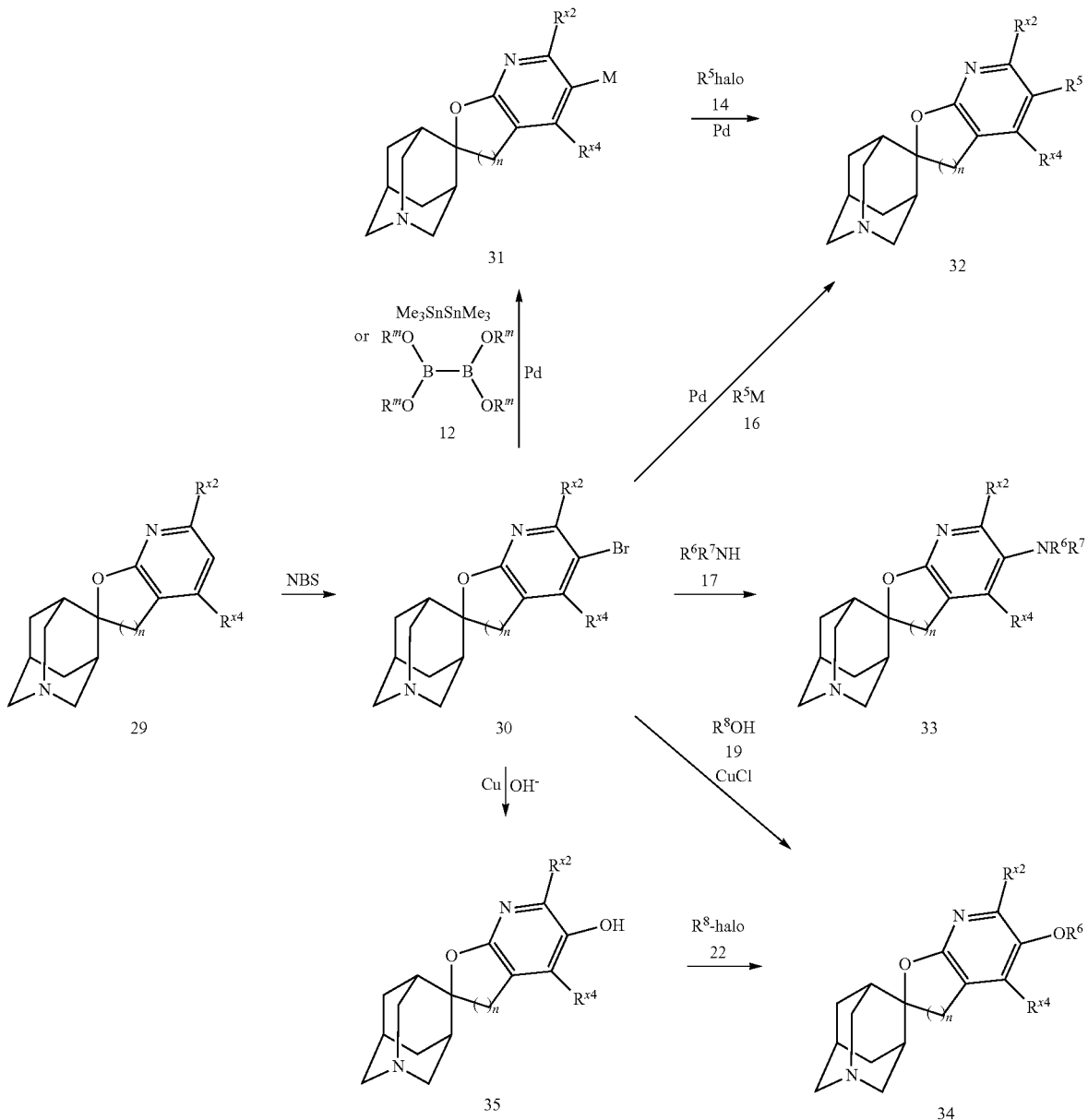

Scheme 5

As outlined in Scheme 5, compounds of formula 29, which may be either the (rs) mixture or the separated individual (r) or (s) isomers, wherein n, $R^{x2}$ and $R^{x4}$ are as defined in formula (1), when treated with reagents such as but not limited to N-bromosuccinimide will provide compounds of formula 30. Compounds of formula 30 when treated with hexamethylditin or an organo-boron compound of formula 12, such as bis(pinacolato)diboron or bis(catecholato)diboron, wherein $R^m$ is hydrogen, alkyl, or aryl, in the presence of a palladium catalyst, such as but not limited to $PdCl_2(PPh_3)_2$ or $PdCl_2$(dppl), will provide the corresponding tin or boronic acid/esters of formula 31, wherein M is $-SnMe_3$ or $-B(OR^m)_2$. Compounds of formula 31 when treated with compounds of formula 14, wherein $R^5$ is an aryl or heteroaryl and halo is bromide, chloride, or iodide, in the presence of a palladium catalyst, such as, but not limited to, $Pd(OAc)_2$, $PdCl_2(PPh_3)_2$, $Pd(PPh_3)_4$, $PdCl_2(dppf)$, or $Pd_2(dba)_3$, will provide compounds of formula 32. Alternatively, compounds of formula 30 when treated with a compound of formula 16, wherein $R^5$ is an aryl or heteroaryl and M is $-SnMe_3$ or $-B(OR^m)_2$ in the presence of a palladium catalyst, such as, but not limited to, $Pd(OAc)_2$, $PdCl_2(PPh_3)_2$, $Pd(PPh_3)_4$, $PdCl_2(dppf)$, or $Pd_2(dba)_3$, will provide compounds of formula 32. Compounds of formula 30 when treated with a compound of formula 17, wherein $R^6$ and $R^7$ are independently selected from H, alkyl, aryl, alkoxycarbonyl, arylcarbonyl, cyclic alkyl, and heteroaryl, in the presence of a ligand, such as but not limited to BINAP, Xantphos, dicyclolexyl(2',4',6'-triisopropylbiphenyl-2-yl)phosphine, dicyclohexyl(2',6'-diisopropoxybiphenyl-2-yl)phosphine, or 2'-(dicyclohexylphosplino)-N,N-dimethylbiphenyl-2-amine, and a palladium catalyst, for example $Pd(OAc)_2$, $PdCl_2(PPh_3)_2$, $Pd(PPh_3)_4$, $PdCl_2(dppf)$ or Pd$_2$(dba)$_3$, with a base, such as, but not limited to, 'BuONa or Cs$_2$CO$_3$ at 110° C. as described in Org. Lett., 2005, 7, 3965, will provide compounds of formula 33. Compounds of formula 30 when treated with an alcohol of formula 19, wherein R$^8$ is alkyl in presence of a base, such as, but not limited to, NaH or 'BuOK, in an organic solvent such as, but not limited to, DMF or THF, will provide compounds of formula 34. Alternatively, compounds of formula 30 when treated with a compound of formula 19, wherein R$^8$ is an aryl group, in the presence of a copper catalyst, such as, but not limited to, Cu, CuCl or CuI, and a ligand, such as, but not limited to, 2,2,6,6-tetramethylheptane-3,5-dione, and Cs$_2$CO$_3$ will provide compounds of formula 34 as described in Org. Lett. 2002, 4, 1623. Alternatively, compounds of formula 30 when treated with an aqueous basic solution, such as, but not limited to, NaOH or KOH, in the presence of a copper catalyst, such as, but not limited to copper, CuCl or CuI, and an amino acid additive, such as, but not limited, to L-pyrroline, at high temperature using microwave heating will provide compounds of formula 35. Compounds of formula 35 when treated with an alkyl halide of formula 22, wherein R$^9$ is an alkyl and halo is chloro, bromo, or iodo, in the presence of a base, such as, but not limited to, Na$_2$CO$_3$, NaH, or NaHMDS will provide compounds of formula 34. Alternatively, compounds of 35 when treated with an aryl halide of formula 22, wherein R$^9$ is aryl and halo is bromo or iodo, in the presence of a copper catalyst, such as, but not limited to, Cu, CuCl or CuI, and a ligand, such as, but not limited to, 2,2,6,6-tetramethylheptane-3,5-dione, and Cs$_2$CO$_3$ will provide compounds of formula 34.

As outlined in Scheme 6, compounds of formula 36, which may be either the (rs) mixture or the separated individual (r) or (s) isomers, wherein n, R$^{x3}$, and R$^{x4}$ are as defined in Formula (1), when treated with m-chloroperbenzoic acid in an organic solvent, such as, but not limited to, dichlormethane or acetonitrile, will provide compounds of formula 37. Compounds of formula 37 when treated with POCl$_3$, which can be heated to facilitate the reaction, will provide compounds of formula 38. Compounds of formula 38 when treated with a compound of formula 16, wherein R$^5$ is aryl or heteroaryl and M is —SnMe$_3$ or —B(OR''')$_2$ in the presence of a palladium catalyst, such as, but not limited to, Pd(OAc)$_2$, PdCl$_2$(PPh$_3$)$_2$, Pd(PPh$_3$)$_4$, PdCl$_2$(dppf), or Pd$_2$(dba)$_3$, will provide compounds of formula 39. Alternatively, when compounds of formula 38 when treated with a compound of formula 17, wherein R$^6$ and R$^7$ are as previously defined, in the presence of a ligand, such as, but not limited to, BINAP, Xantphos, dicyclohexyl(2',4',6'-triisopropylbiphenyl-2-yl)phosphine, dicyclohexyl(2',6'-diisopropoxybiphenyl-2-yl)phosphine, or 2'-(dicyclohexylphosphino)-N,N-dimethylbiphenyl-2-amine, and a palladium catalyst, such as, but not limited to, Pd(OAc)$_2$, PdCl$_2$(PPh$_3$)$_2$, Pd(PPh$_3$)$_4$, PdCl$_2$(dppf, or Pd$_2$(dba)$_3$, with a base, such as, but not limited to, 'BuONa or Cs$_2$CO$_3$ at 110° C. as described in Org. Lett., 2005, 7, 3965, will provide compounds of formula 40. Compounds of formula 38 when treated with an alcohol of formula 19, wherein R$^8$ is as previously defined, in presence of a base, such as, but not limited to, NaH or 'BuOK, will provide compounds of formula 41.

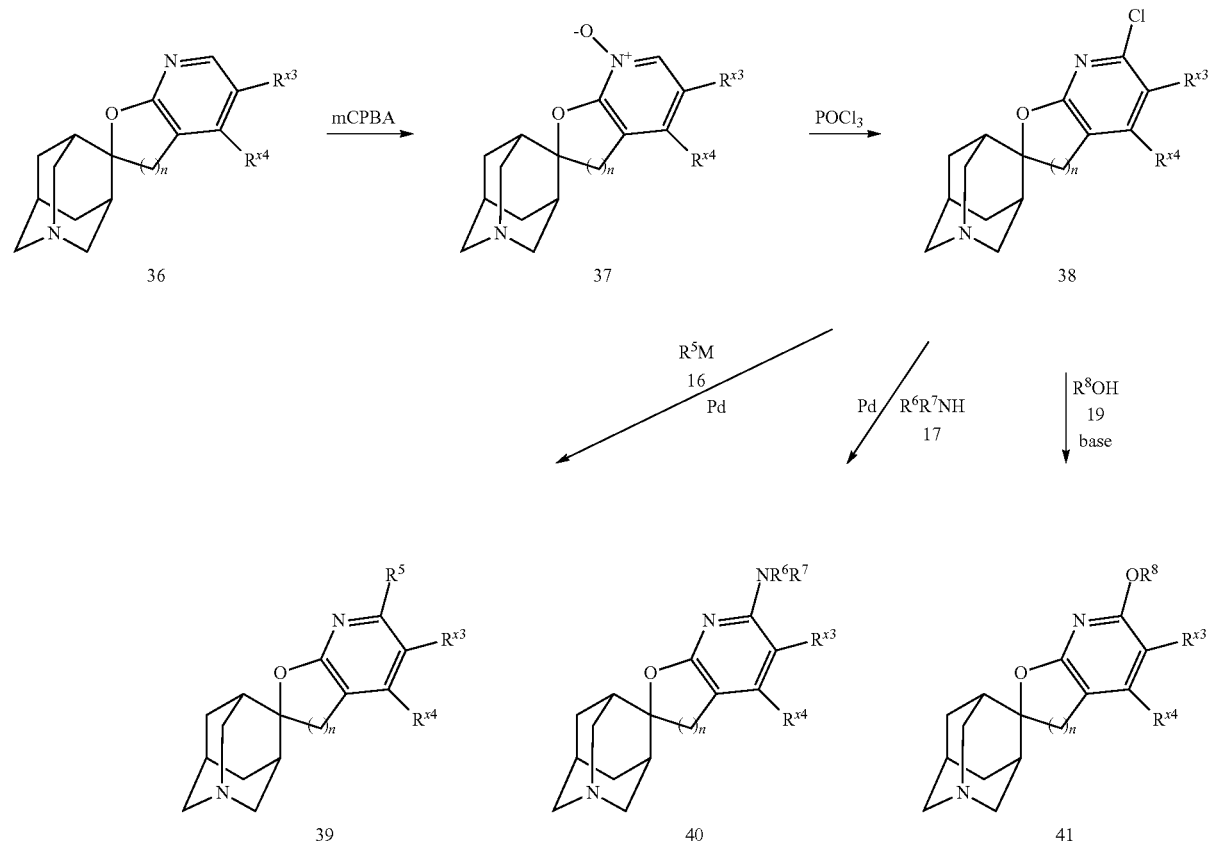

Scheme 6

Scheme 7

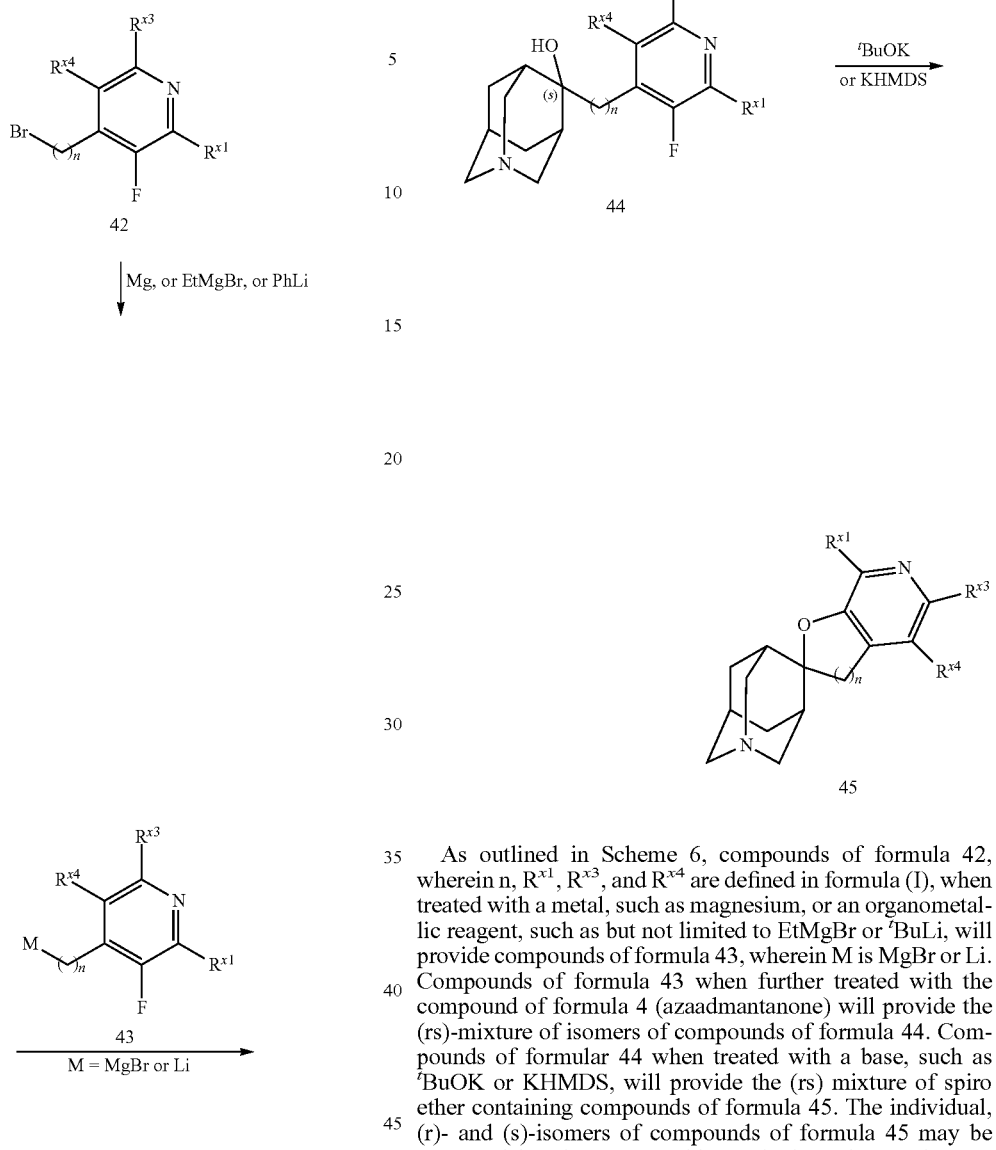

As outlined in Scheme 6, compounds of formula 42, wherein n, $R^{x1}$, $R^{x3}$, and $R^{x4}$ are defined in formula (I), when treated with a metal, such as magnesium, or an organometallic reagent, such as but not limited to EtMgBr or $^tBuLi$, will provide compounds of formula 43, wherein M is MgBr or Li. Compounds of formula 43 when further treated with the compound of formula 4 (azaadmantanone) will provide the (rs)-mixture of isomers of compounds of formula 44. Compounds of formular 44 when treated with a base, such as $^tBuOK$ or KHMDS, will provide the (rs) mixture of spiro ether containing compounds of formula 45. The individual, (r)- and (s)-isomers of compounds of formula 45 may be seperated by chromatographic methods as known by one skilled in the art.

Scheme 8

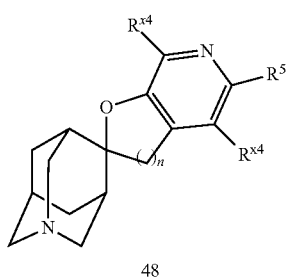

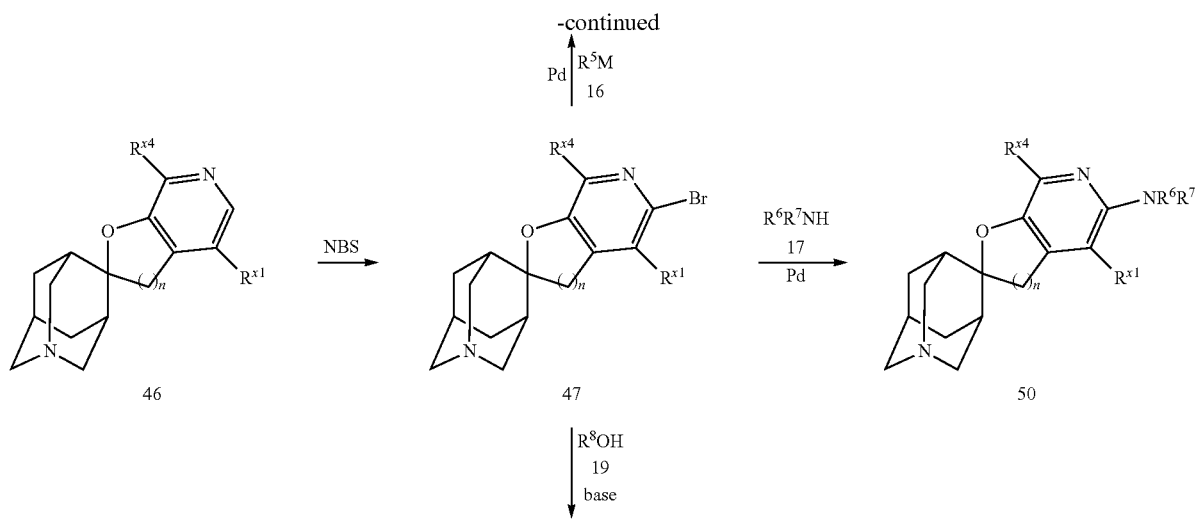

As outlined in Scheme 8, compounds of formula 46, which may be either the (rs) mixture or the separated individual (r)- or (s)-isomers, wherein n, $R^{x1}$, and $R^{x4}$ are as defined in formula (I), when treated with N-bromosuccinimide will provide compounds of formula 47. Compounds of formula 47 when treated with compounds of formula 16 wherein $R^5$ and M are as defined in Scheme 3, in the presence of a palladium catalyst, such as, but not limited to, Pd(OAc)$_2$, PdCl$_2$(PPh$_3$)$_2$, Pd(PPh$_3$)$_4$, PdCl$_2$(dppf), or Pd$_2$(dba)$_3$, will provide compounds of formula 48. Compounds of formula 47 when treated with a compound of formula 17, wherein $R^6$ and $R^7$ are as defined in Scheme 3, in the presence of a ligand, such as, but not limited to, BINAP, Xantphos, dicyclohexyl(2',4',6'-triisopropylbiphenyl-2-yl)phosphine, dicyclohexyl(2',6'-diisopropoxybiphenyl-2-yl)phosphine, or 2'-(dicyclohexylphosphino)-N,N-dimethylbiphenyl-2-amine, and a palladium catalyst, such as, but not limited to, Pd(OAc)$_2$, PdCl$_2$(PPh$_3$)$_2$, Pd(PPh$_3$)$_4$, PdCl$_2$(dppf), or Pd$_2$(dba)$_3$, and a base, such as, but not limited to, $^t$BuONa or Cs$_2$CO$_3$, at 110° C. as described in Org. Lett., 2005, 7, 3965, will provide compounds of formula 50. Compounds of formula 47 when treated with a compound of formula 19, wherein $R^8$ is as defined in Scheme 3, in presence of a base, such as, but not limited to, NaH or $^t$BuOK, will provide compounds of formula 51.

Scheme 9

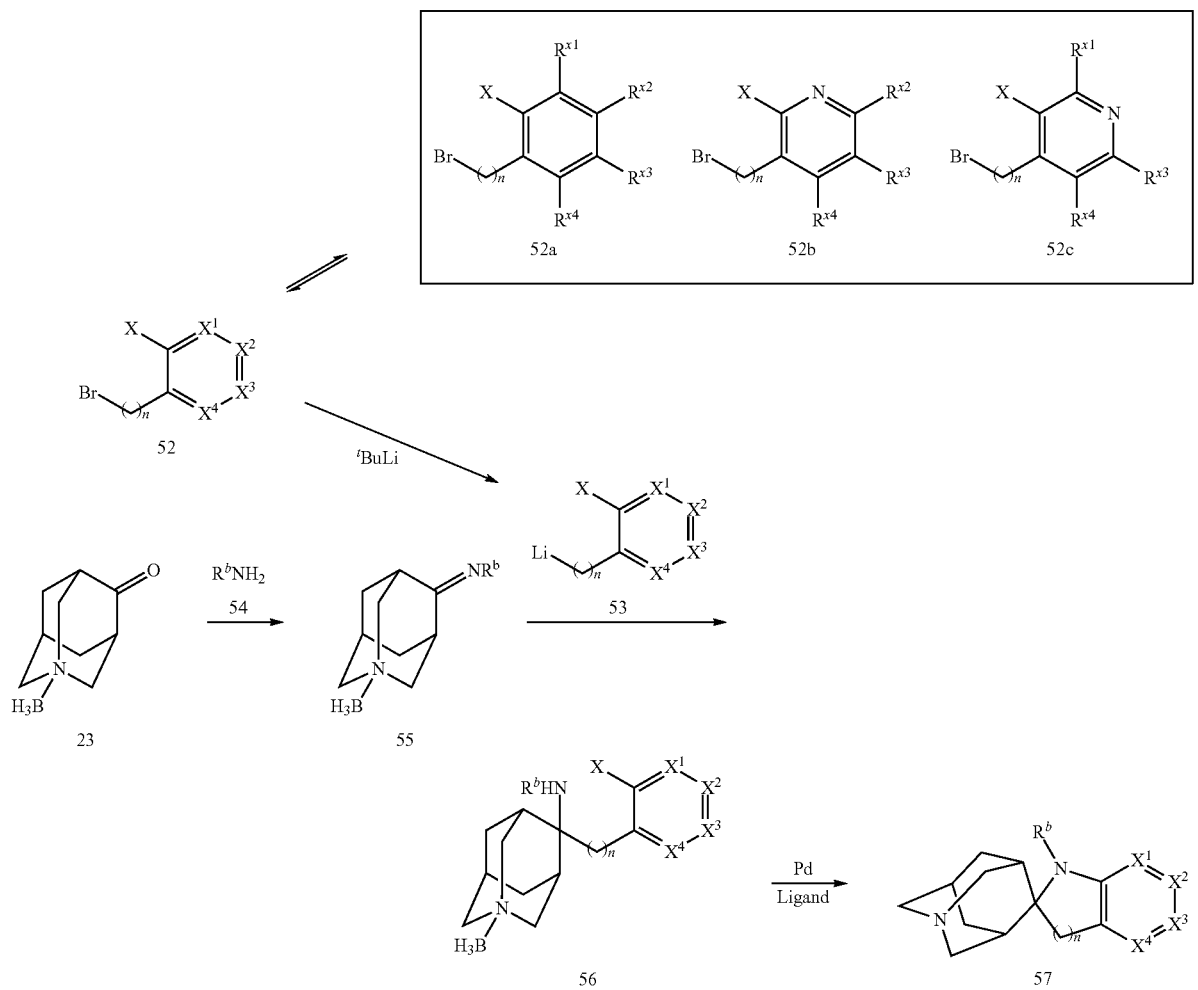

As outlined in Scheme 9, compounds of formula 52, wherein n, $X^1$, $X^2$, $X^3$, and $X^4$ are as defined in formula (I), and X is chloro or bromo, when treated with $^t$BuLi, will provide compounds of formula 53. Compounds of formula 23 when treated with compounds of formula 54, wherein $R^b$ is as defined in formula (I), will provide compounds of formula 55, Compounds of formula 55 when is further treated with a compound of formula 53, will provide compounds of formula 56. Compounds of formula 56 will cyclize to provide compound of formula 57, in the presence of a palladium catalyst, such as, but not limited to, Pd(OAc)$_2$, PdCl$_2$(PPh$_3$)$_2$, Pd(PPh$_3$)$_4$, PdCl$_2$(dppf), or Pd$_2$(dba)$_3$, a ligand, such as but not limited to BINAP, Xantphos, dicyclolexyl(2',4',6'-triisopropylbiphenyl-2-yl)phosphine, dicyclohexyl(2',6'-diisopropoxybiphenyl-2-yl)phosphine, or 2'-(dicyclohexylphosphino)-N,N-dimethylbiphenyl-2-amine, and a base, such as but not limited to $^t$BuONa or Cs$_2$CO$_3$ at 110° C. as described in Org. Lett. 2005, 7, 3965.

Scheme 10

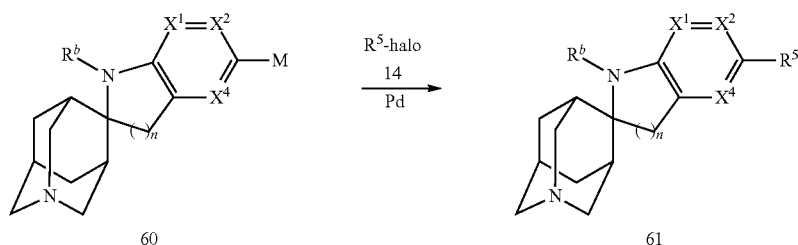

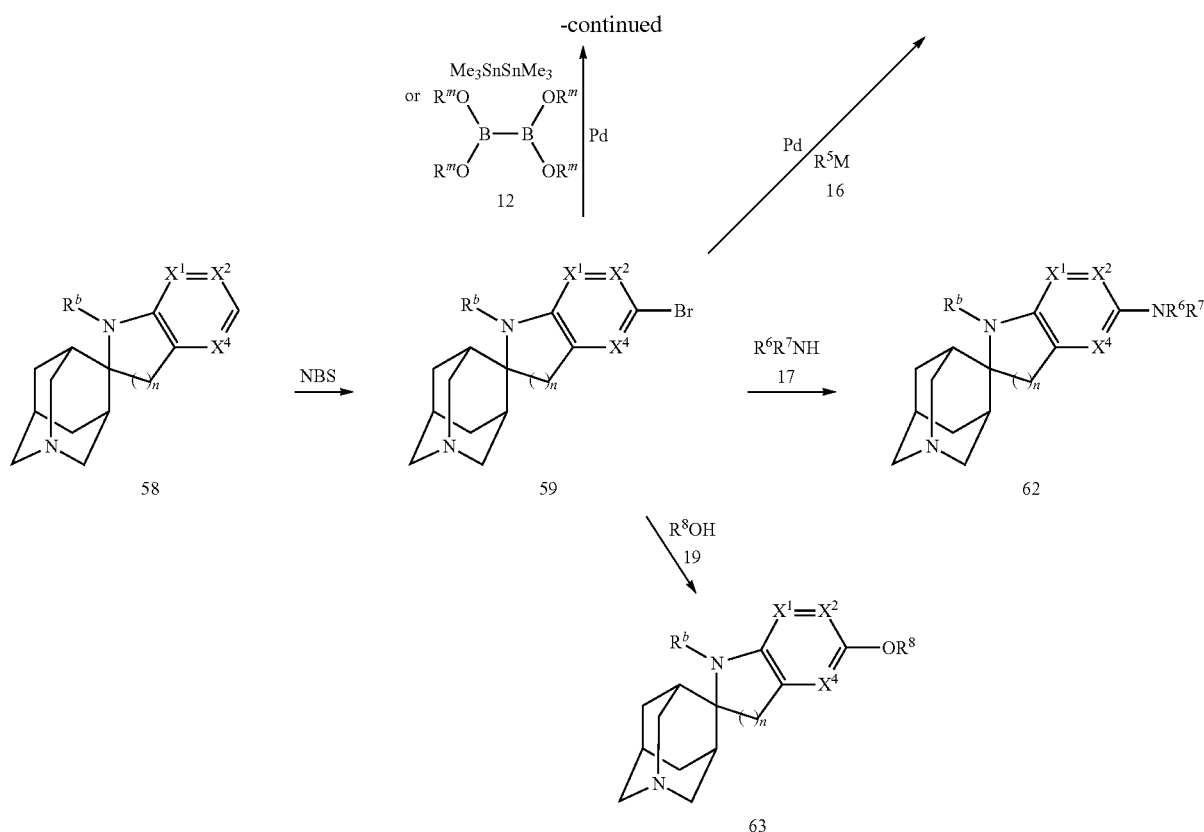

As outlined in Scheme 10, compounds of formula 58, which may be either the (rs) mixture or the separated individual (r) or (s) isomers, wherein n, $R^b$, $X^1$, $X^2$, and $X^4{}_4$ are as defined in formula (I), when treated with N-bromosuccinimide will provide compound of formula 59. Compound of formula 59 when treated with hexamethylditin, or an organoboron compound of formula 12, in the presence of a palladium catalyst such as, but not limited to, $PdCl_2(PPh_3)_2$ or $PdCl_2(dppf)$, will provide the corresponding tin or boronic acid/esters of formula 60, wherein M is $—SnMe_3$ or $—B(OR^m)_2$. Compounds of formula 60 when treated with compounds of formula 14 wherein $R^5$ and halo are as defined in Scheme 7, in the presence of a palladium catalyst, such as but not limited to $Pd(OAc)_2$, $PdCl_2(PPh_3)_2$, $Pd(PPh_3)_4$, $PdCl_2$ (dppf) or $Pd_2(dba)_3$, will provide compounds of formula 61. Alternatively, compounds of formula 59 when treated with compound of formula 16, described in Scheme 3, in the presence of a palladium catalyst, such as but not limited to, $Pd(OAc)_2$. $PdCl_2(PPh_3)_2$, $Pd(PPh_3)_4$, $PdCl_2(dppf)$, or $Pd_2(dba)_3$, will provide compounds of formula 61. Compound of formula 59 when treated with compound of formula 17, wherein $R^6$ and $R^7$ are as defined in Scheme 3, in the presence of a ligand, such as but not limited to BINAP, Xantphos, dicyclohexyl(2',4',6'-triisopropylbiphenyl-2-yl)phosphine, dicyclohexyl(2',6'-diisopropoxybiphenyl-2-yl)phosphine, or 2'-(dicyclohexylphosphino)-N,N-dimethylbiphenyl-2-amine, and a palladium catalyst, such as but not limited to, $Pd(OAc)_2$, $PdCl_2(PPh_3)_2$, $Pd(PPh_3)_4$, $PdCl_2(dppf)$, or $Pd_2(dba)_3$, and a base, such as, but not limited to, $^tBuONa$ or $Cs_2CO_3$ at 110° C. as described in Org. Lett., 2005, 7, 3965, will provide compounds of formula 62. Compound of formula 59 when treated with the compound of formula 19, wherein $R^8$ is as described in Scheme 3, according to the method described in Scheme 3, will provide compound of formula 63.

Scheme 11

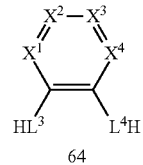

4
acid
→

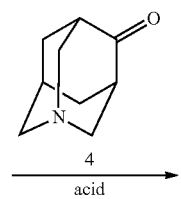

64

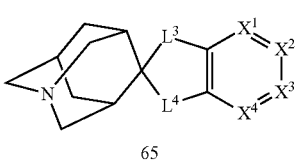

65

$L^3$, $L^4$ = O, or $NR^b$

As shown in Scheme 11, the compound of formula 64, wherein $L^3$ and $L^4$ are each independently selected from group consisting of O and $NR^b$, and $R^b$, $X^1$, $X^2$, $X^3$, and $X^4$ are as defined in formula (I), when treated with compound of formula 4, in the presence of an acid, such as but not limited to p-toluenesulfonic acid, will provide compound of formula 65.

Scheme 12

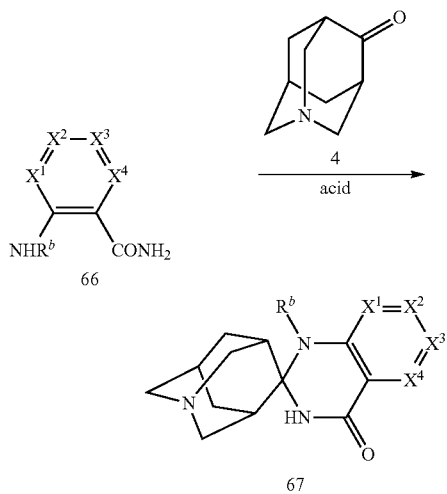

As shown in Scheme 12, the compound of formula 66, wherein $R^b$, $X^1$, $X^2$, $X^3$, and $X^4$ are as defined in formula (I), when treated with compound of formula 4, in the presence of an acid, such as but not limited to p-toluenesulfonic acid will provide compound of formula 67.

In addition, compounds of formula (II), (III), and (IV) may be converted to an N-oxide compounds of formula (I) by treatment with an oxidizing agent. Examples of the oxidizing agent include, but not limited to, aqueous hydrogen peroxide and m-chloroperbenzoic acid. The reaction is generally performed in a solvent such as, but not limited to, acetonitrile, water, dichloromethane, acetone, or mixture thereof, preferably a mixture of acetonitrile and water, at a temperature from about 0° C. to about 80° C. for a period of about 1 hour to about 4 days.

The compounds and intermediates of the invention may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation tinder vacuum, and trituration, as described for instance in "Vogel's Textbook of Practical Organic Chemistry". 5th edition (1989), by Furniss, Hannaford, Smith, and Tatchell, pub. Longman Scientific & Technical. Essex CM20 2JE, England.

The compounds of the invention contain at least one basic nitrogen whereby the compound can be treated with an acid to form a desired salt. For example, a compound may be treated with an acid at or above room temperature to provide the desired salt, which is deposited, and collected by filtration after cooling. Examples of acids suitable for the reaction include, but are not limited to, tartatic acid, lactic acid, succinic acid, as well as mandelic, atrolactic, methanesulfonic, ethanesulfonic, toluenesulfonic, naphthalenesulfonic, carbonic, fumaric, gluconic, acetic, propionic, salicylic, hydrochloric, hydrobromic, phosphoric, sulfuric, citric, or hydroxybutyric acid, camphorsulfonic, malic, phenylacetic, aspartic, glutamic, and the like.

The compounds of the invention and processes for making compounds for the method of the invention will be better understood by reference to the following Examples, which are intended as an illustration of and not a limitation upon the scope of the invention.

EXAMPLES

Example 1

3H-(4's)-1'-Azaspiro[benzofuran-2,4']-tricyclo[3.3.1.1$^{3,7}$]decane bis(hydrochloric acid)

Example 1A (4s)- and (4r)-4-(2-Fluorobenzyl)-1-azatricyclo[3.3.1.1$^{3,7}$]decan-4-ol Magnesium turning (Aldrich, 2.40 g, 0.1 mmol) and $I_2$ (Aldrich, 10 mg) were combined in diethyl ether (Aldrich, anhydrous, 20 mL) and treated with 1-(bromomethyl)-2-fluorobenzene (Aldrich, 18.9 g, 0.1 mol) in diethyl ether (Aldrich, anhydrous, 200 mL) at ambient temperature under $N_2$. After the reaction was initiated (discharge of iodine brown color), the addition of 1-(bromomethyl)-2-fluorobenzene ether solution was continued to maintain the reaction temperature ≦30° C. After the addition was completed, the mixture was stirred at ambient temperature for 4 h. 1-Azatricyclo[3.3.1.1$^{3,7}$]decan-4-one (ref. *Synthesis,* 1992, 1080-1082, 7.60 g, 50 mmol) in diethyl ether (Aldrich, anhydrous, 50 mL) was added at 0-5° C. The reaction mixture was then stirred at ambient temperature for 10 h. It was then qunched with saturated $NH_4Cl$ (20 mL) at 5-10° C. and extracted with $CHCl_3$ (3×100 mL). The combined extracts were concentrated and the residue was purified with chromatography ($SiO_2$, $CHCl_3$/MeOH (with 2 v. % $NH_3.H_2O$)=90/10). The upper spot ($R_f$=0.25) was isolated (4.71 g, yield. 36.1%) and confirmed as (4s)-stereoisomer, of the title compound. The lower spot ($R_f$=0.10) was obtained (3.33 g, yield, 17.9%) and confirmed as (4r)-stereoisomer of the title compound. (4s)-4-(2-Fluorobenzyl)-1-azatricyclo[3.3.1.1$^{3,7}$]decan-4-ol: $^1$H NMR (300 MHz, $CD_3OD$) δ ppm 1.50-1.63 (m, 3 H), 1.68-1.84 (m, 2 H), 2.33-2.53 (m, 2 H)-3.05-3.11 (m, 4 H), 3.16 (d, J=13.90 Hz, 2 H), 3.43 (d, J=13.56 Hz, 2 H), 6.97-7.07 (m, 1 H), 7.10 (dd, J=7.46, 1.02Hz, 1 H), 7.17-7.28 (m, 1 H), 7.35 (td, J=7.63, 1.70 Hz, 1 H); MS (DCI/$NH_3$) m/z=262 (M+H)$^+$; (4r)-4-(2-Fluorobenzyl)-1-azatricyclo[3.3.1.1$^{3,7}$]decan-4-ol: $^1$H NMR (300 MHz, $CD_3OD$) δ ppm 1.47-1.64 (m, 2 H), 1.66-1.80 (m, 1 H), 1.96-2.12 (m, 2 H), 2.26-2.45 (m, 2 H), 2.86 (d, J=12.55 Hz, 2 H), 3.02-3.14 (m, 4 H), 3.54 (d, J=12.55 Hz, 2 H), 6.98-7.04 (m, 1 H), 7.08 (td, J=7.46, 1.36 Hz, 1 H), 7.17-7.27 (m, 1 H), 7.35 (td. J=7.54, 1.86 Hz, 1 H); MS (DCI/$NH_3$) m/z=262 (M+H)$^+$.

Example 1B 3H-(4's)-1'-Azaspiro[benzofuran-2,4']-tricyclo[3.3.1.1$^{3,7}$]decane The (4s)-stereoisomer of Example 1A (4.50 g, 17.2 mmol) was treated with $^t$BuOK (Aldrich, 2.24 g 20 mmol) in THF (Aldrich, anhydrous, 100 mL) at 65° C. for 50 h. It was then cooled down to ambient temperature and qunched with water (10 mL). The reaction mixture was extracted with $CHCl_3$ (3×100 mL). The combined extracts were concentrated and the residue was purified with chromatography ($SiO_2$, $CHCl_3$/MeOH (with 2 v. % $NH_3.H_2O$)=90/10, $R_f$=0.20) to give the title compound (3.34 g, yield, 80.6%). $^1$H NMR (300 MHz, DMSO-$D_6$) δ ppm 1.46-1.59 (m, 1 H), 1.63-1.73 (m, 2 H), 1.74-1.90 (m, 2 H), 2.25-2.40 (m, 2 H), 2.93-3.15 (m, 7 H), 3.27-3.29 (m, 1 H), 6.71-6.82 (m, 2 H), 7.06 (td, J=7.71, 1.53 Hz, 1 H), 7.16 (dd, J=7.12, 1.02 Hz, 1 H); MS (DCI/NH$_3$) m/z=242 (M+H)$^+$.

Example 1C 3H-(4's)-1'-Azaspiro[benzofuran-2,4']-tricyclo[3.3.1.1$^{3,7}$]decane bis(hydrochloric acid)

The product of Example 1B (80 mg, 0.33 mmol) was treated with HCl (Aldrich, 4 M in dioxane, 0.2 mL. 0.8 mmol) in EtOAc (5 mL) at ambient temperature for 10 h to give the title compound (75 mg, yield, 72.8%). $^1$H NMR (300 MHz, CD$_3$OD) δ ppm 1.98 (d, J=13.22 Hz, 2 H), 2.12-2.29 (m, 3 H), 2.54 (d, J=13.22 Hz, 2 H), 3.27-3.30 (m, 2 H), 3.55-3.60 (m, 2 H), 3.61-3.68 (m, 4 H), 6.79 (d, J=7.80 Hz, 1 H), 6.85 (t, J=7.46 Hz, 1 H), 7.11 (t, J=7.12 Hz, 1 H), 7.19 (d, J=7.46 Hz, 1 H), MS (DCI/NH$_3$) m/z=242 (M+H)$^+$, Anal. Calc. for C$_{16}$H$_{19}$NO. 1.89HCl: C, 61.94; H, 6.79: N, 4.51; Found: C, 61.54; H, 6.64: N, 4.32.

Example 2

3H-(4's)-1'-Azaspiro[5-bromobenzofuran-2,4']-tricyclo[3.3.1.1$^{3,7}$]decane hydrochloric acid Example 2A 3H-(4's)-1'-Azaspiro[5-bromobenzofuran-2,4']-tricyclo[3.3.1.1$^{3,7}$]decane The product of Example 1B (2.07 g, 8.6 mmol) was treated with N-bromosuccinimide (NBS) (Aldrch, 2.30 g, 12.9 mmol) in MeCN/HOAc (v. 5/1, 70 mL) at 0° C. to ambient temperature for 6 h. After the reaction was completed, it was quenched with water (5.0 mL) and concentrated. The residue was basified with saturated Na$_2$CO$_3$ until pH=9-10. The mixture was then extracted with CHCl$_3$ (3×50 mL). The combined extracts were concentrated and the residue was purified with chromatography (SiO$_2$, CHCl$_3$/MeOH (with 2 v. % NH$_3$.H$_2$O)=90/10, R$_f$=0.25) to give the title compound (2.50 g. yield, 90.8%). $^1$H NMR (300 MHz, DMSO-D$_6$) δ ppm 1.56-1.73 (m, 1 H), 1.77-1.84 (m, 2 H), 1.85-1.98 (m, 2 H), 2.33-2.59 (m, 2 H), 3.02-3.26 (m, 8 H), 6.66 (d, J=8.48 Hz, 1 H), 7.18 (dd, J=8.48, 2.37 Hz, 1 H), 7.29 (d, J=2.03 Hz, 1 H); MS (DCl/NH$_3$) m/z=320 (M+H)$^+$, 322 (M+H)$^+$.

Example 2B 3H-(4's)-1'-Azaspiro[5-bromobenzofuran-2,4']-tricyclo[3.3.1.3$^{3,7}$]decane hydrochloric acid The product of Example 2A (80 mg, 0.25 mmol) was treated with HCl (Aldrich, 4 M in dioxane, 0.2 mL, 0.8 mmol) in EtOAc (5 mL) at ambient temperature for 10 h to give the title compound (60 mg, yield, 67.3%). $^1$H NMR (300 MHz, CD$_3$OD) δ ppm 1.87-2.06 (m, 2 H), 2.12-2.34 (m, 3 H), 2.39-2.63 (m, 2 H), 3.26-3.39 (m, 2 H), 3.52-3.60 (m, 2 H), 3.59-3.75 (m, 4 H), 6.73 (d, J=8.48 Hz, 1 H), 7.25 (dd, J=8.48, 2.37 Hz, 1 H), 7.34 (d, J=2.03 Hz, 1 H); MS (DCI/NH$_3$) m/z=320 (M+H)$^+$. 322 (M+H)$^+$, Anal. Calc. for C$_{16}$H$_{18}$BrNO.1.00HCl.0.20H$_2$O: C. 53.34: H, 5.34; N. 3.89; Found: C, 53.22; H, 5.30; N, 3.79.

Example 3

3H-(4's)-1'-Azaspiro[5-phenylbenzofuran-2,4']-tricyclo[3.3.1.1$^{3,7}$]decane hydrochloric acid Example 3A 3H-(4's)-1'-Azaspiro[5-phenylbenzofuran-2,4']-tricyclo[3.3.1.1$^{3,7}$]decane The product of Example 2A (200.0 mg 0.625 mmol) was coupled with phenyl-boronic acid (Aldrich, 113 mg, 0.94 mmol) under the catalysis of Pd(PPh$_3$)$_4$ (Aldrich, 14.4 mg. 0.0125 mmol) in 1,4-dioxane (5.0 mL) and K$_2$CO$_3$ (2M, 1 mL) at 90° C. for 3 h. Upon completion of the reaction, the mixture was diluted with CHCl$_3$ (10 mL), washed with brine (2×2 mL), the organonic solution was concentrated. The residue was purified by preparative HPLC [Waters® XTerra RP18 column, 5μ, 30×100 mm, flow rate 40 mL/minute, 5-95% gradient of acetonitrile in buffer (0.1 M aqueous ammonium bicarbonate, adjusted to pH 10 with ammonium hydroxide), with UV detection at 254 nm]. Fractions containing the desired product were pooled, concentrated under vacuum, diluted with methanol or ethyl acetate, and filtered to afford the title compound (80 mg, yield, 41%). $^1$H NMR (300 MHz, CD$_3$OD) δ ppm 1.63-1.78 (m, 1 H), 1.79-1.99 (m, 4 H), 2.38-2.68 (m, 2 H), 3.07-3.27 (m, 8 H), 6.80 (d, J=8.14 Hz, 1 H), 7.19-7.28 (m, 1H), 7.30-7.45 (m, 4 H), 7.48-7.61 (m, 2 H); MS (DCI/NH$_3$) m/z=318 (M+H)$^+$.

Example 3B 3H-(4's)-1'-Azaspiro[5-phenylbenzofuran-2,4']-tricyclo[3.3.1.1$^{3,7}$]decane hydrochloric acid The product of Example 3A (80 mg, 0.25 mmol) was treated with HCl (Aldrich, 4 M in dioxane. 0.1 mL, 0.4 mmol) in EtOAc (5 mL) at ambient temperature for 10 h to give the title compound (85 mg, yield, 87.6%). $^1$H NMR (300 MHz, CD$_3$OD) δ ppm 1.87-2.06 (m, 2 H), 2.12-2.34 (m, 3 H), 2.39-2.63 (m, 2 H), 3.26-3.39 (m, 2 H), 3.52-3.60 (m, 2 H), 3.59-3.75 (m, 4 H), 6.73 (d, J=8.48 Hz, 1 H), 7.25 (dd, J=8.48, 2.37 Hz, 1 H), 7.34 (d, J=2.03 Hz, 1 H); MS (DCI/NH$_3$) m/z=318 (M+H)$^+$. Anal. Calc. for C$_{22}$H$_{23}$NO 1.25HCl: C, 72.79; H, 6.73; N, 3.86; Found: C, 72.55; H, 6.68; N, 3.66.

Example 4

3H-(4's)-1'-Azaspiro[5-(indol-5-yl)-benzofuran-2,4']-tricyclo[3.3.1.1$^{3,7}$]decane The product of Example 2A (200.0 mg 0.625 mmol) was coupled with indol-5-yl boronic acid (Frontier, 150 mg, 0.94 mmol) according to the procedure of Example 3A to give the title compound (110 mg, yield. 49.4%), $^1$H NMR (300 MHz, CD$_3$OD) δ ppm 1.87-2.08 (m, 3 H), 2.08-2.22 (m, 2 H), 2.41-2.69 (m, 2 H), 3.33-3.36 (m, 2 H), 3.39-3.52 (m, 6 H), 6.45 (dd, J=3.05, 0.68 Hz. 1 H), 6.82 (d, J=8.14 Hz, 1 H), 7.23 (d, J=3.05 Hz, 1 H), 7.28 (dd, J=8.50, 1.70 Hz, 1 H), 7.34-7.44 (m, 2 H), 7.45 (s, 1 H), 7.67 (d, J=1.70 Hz, 1 H); MS (DCI/NH3) m/z=357 (M+H)$^+$.

Example 5

3H-(4's)-1'-Azaspiro[5-(indol-6-yl)-benzofuran-2,4']-tricyclo[3.3.1.1$^{3,7}$]decane The product of Example 2A (300 mg, 0.98 mmol) was coupled with indol-6-yl boronic acid (Frontier, 300 mg, 1.86 mmol) according to the procedure of Example 3A to give the title compound solid (17.3 mg, yield, 4.9%). $^1$H NMR (300 MHz, CD$_3$OD) δ ppm 1.57-1.79 (m, 1 H), 1.82-2.04 (m, 4 H), 2.29-2.65 (m, 2 H), 3.11-3.28 (m, 8 H), 6.42 (dd, J=3.05, 0.68 Hz, 1 H), 6.79 (d, J=8.48 Hz, 1 H), 7.16-7.25 (m, 2 H), 7.37 (dd, J=8.14, 2.03 Hz, 1 H), 7.45 (s, 1 H), 7.51 (s, 1 H), 7.54 (d, J=8.48 Hz, 1 H); MS (DCI/NH$_3$) m/z 357(M+1)$^+$.

Example 6

3H-(4's)-1'-Azaspiro[5-(indol-4-yl)-benzofuran-2,4']-tricyclo[3.3.1.1$^{3,7}$]decane trifluoroacetate The product of Example 2A (200 mg. 0.625 mmol) was coupled with indolyl-4-boronic acid (150 mg. 0.94 mmol: Frontier) under the catalysis of PdCl$_2$(PPh$_3$)$_2$ (Aldrich. 7.0 mg. 0.01 mmol.) and biphenyl-2-yl-dicyclohexyl-phosphane (Aldrich, 10.5 mg. 0.03 mmol) in dioxane/EtOH/Na$_2$CO$_3$ (aq, 1 M) (v. 1/1/1, 3 mL) at 150° C. (150 watts max.) for 15 min in an Emry™ Creator microwave. The inorganic solid was filtered off with a syringe filter and the liquid mixture was purified by preparative HPLC (Gilson, column, Xterra® 5 µm, 40×100 mm: eluting Solvent, MeCN/H$_2$O (with 0.1v. % TFA) (v. 90/10 to 10/90 over 25 min.); flow rate, 40 mL/min., uv, 254 nm), fractions of the desired product were collected and concentrated, the residue was stirred in Et$_2$O/EtOH (v. 10/1, 5 mL) for 16 h, to give the title compound as solid (13.5 mg, yield, 4.2%). $^1$H NMR (300 MHz, DMSO-D$_6$) δ ppm 1.79-2.01 (m, 2 H), 2.07-2.18 (m, 1 H), 2.19-2.38 (m, 4 H), 3.34-3.40 (m, 2 H), 3.43-3.68 (m, 6 H), 6.48-6.59 (m, 1 H), 6.93 (d, J=8.14 Hz, 1 H), 6.99 (dd, J=7.12, 1.02 Hz, 1 H), 7.14 (t, J=7.10 Hz, 1 H), 7.33-7.39 (m, 2 H), 7.42 (dd, J=8.31, 1.86 Hz, 1 H), 7.47 (s, 1 H), 11.2 (s, 1 H); MS (DCI/NH$_3$) m/z 357(M+1)$^+$; Anal. calcd. for C$_{24}$H$_{24}$N$_2$O-1.20CF$_3$CO$_2$H-1; C. 64.28; H, 5.15; N, 5.68. Found: C, 64.52; H, 4.90; N. 5.81.

Example 7

3H-(4'r)-1'-Azaspiro[benzofuran-2,4']-tricyclo[3.3.1.1$^{3,7}$]decane hydrochloric acid

Example 7A 3H-(4'r)-1'-Azaspiro[benzofuran-2,4']-tricyclo[3.3.1.1$^{3,7}$]decane Prepared from the (4r)-stereoisomer of Example 1A (3.11 g, 1.9 mmol) and $^t$BuOK (Aldrich, 1.68 g, 15 mmol) according to the procedure of Example 1B (1.23 g, Yield. 42.9%). $^1$H NMR (300 MHz, DMSO-D$_6$) δ ppm 1.49-1.61 (m, 1 H), 1.61-1.73 (m, 2 H), 1.89-2.07 (m, 4 H), 2.85-2.90 (m, 1 H), 2.90-2.94 (m, 1 H), 2.95-3.00 (m, 2 H), 3.12-3.15 (m, 2 H), 3.34-3.43 (m, 2 H), 6.73-6.80 (m, 2 H), 7.06 (td, J=7.80, 1.36 Hz, 1 H), 7.17 (d, J=7.12 Hz, 1 H); MS (DCI/NH$_3$) m/z=242 (M+H)$^+$.

Example 7B 3H-(4'r)-1'-Azaspiro[benzofuran-2,4']-tricyclo[3.3.1.1$^{3,7}$]decane hydrochloric acid The product of Example 1B (80 mg. 0.33 mmol) was treated with HCl (Aldrich, 4 M in dioxane, 0.2 mL, 0.8 mmol) in EtOAc (5 mL) at ambient temperature for 10 h to give the title compound (70 mg, yield. 76.4%). $^1$H NMR (300 MHz, CD$_3$OD) δ ppm 2.04-2.39 (m, 7 H), 3.30-3.35 (m, 2 H), 3.45-3.69 (m, 4 H), 3.93 (d, J=11.87 Hz, 2 H), 6.78 (d, J=8.14 Hz, 1 H), 6.86 (td, J=7.46, 1.02 Hz. 1 H), 7.11 (td, J=7.97, 1.02 Hz, 1 H), 7.21 (dd, J=7.46, 1.02 Hz, 1 H); MS (DC/NH$_3$) m/z-=242 (M+H)$^+$, Anal. Calc. for C$_{16}$H$_{19}$NO.1.00HCl.0.10H$_2$O; C, 68.731 H, 7.28; N, 5.01; Found; C, 68.67; H, 7.23; N, 4.92.

Example 8

3H-(4'r)-1'-Azaspiro[5-bromobenzofuran-2,4']-tricyclo[3.3.1.1$^{3,7}$]decane hydrochloric acid

Example 8A 3H-(4'r)-1'-Azaspiro[5-bromobenzofuran-2,4']-tricyclo[3.3.1.1$^{3,7}$]decane Prepared from the product or Example 7A (1.20 g, 5.0 mmol) and N-bromosuccinimide (NBS) (Aldrch. 1.34, 7.5 mmol) according to the procedure of Example 2A (1.25 g, yield, 78.1%). $^1$H NMR (300 MHz, DMSO-D$_6$) δ ppm 1.63-1.74 (m, 1 H), 1.76-1.85 (m, 2 H), 1.96-2.19 (m, 4 H), 3.03 (d, J=12.89 Hz, 2 H), 3.09-3.16 (m, 2 H), 3.18-3.24 (m, 2 H), 3.56 (d, J=12.55 Hz. 2 H), 6.66 (d, J=8.48 Hz, 1 H), 7.18 (dd. J=8.48, 2.03 Hz, 1 H), 7.27-7.30 (m, 1 H); MS (DCI/NH$_3$) m/z=320 (M+H)$^+$. 322 (M+H)$^+$.

Example 8B 3H-(4'r)-1'-Azaspiro[5-bromobenzofuran-2,4']-tricyclo[3.3.1.1$^{3,7}$]decane hydrochloric acid The product of Example 8A (70 mg, 0.22 mmol) was treated with HCl (Aldrich, 4 M in dioxane, 0.1 mL, 0.4 mmol) in EtOAc (5 mL) at ambient temperature for 10 h to give the title compound (60 mg, yield, 76.5%). $^1$H NMR (300 MHz, CD$_3$OD) δ ppm 2.02-2.40 (m, 7 H), 3.32-3.34 (m, 2 H), 3.50 (d, J=12.55 Hz, 2 H), 3.54-3.58 (m, 2 H), 3.91 (d, J=11.87 Hz, 2 H), 6.73 (d, J=8.48 Hz, 1 H), 7.25 (dd, J=8.48, 2.03 Hz, 1 H), 7.33-7.41 (m, 1 H); MS (DCI/NH$_3$) m/z=320 (M+H)$^+$, 322 (M+H)$^+$. Anal. Calc. for C$_{16}$H$_{18}$BrNO. 1.00HCl0.50H$_2$O; C, 52.554; H, 5.51; N, 3.83; Found; C, 52.21; H, 5.490; N. 3.61.

Example 9

3H-(4'r)-1'-Azaspiro[5-phenylbenzofuran-2,4']-tricyclo[3.3.1.1$^{3,7}$]decane

Prepared from the product of Example 7A (160 mg 0.50 mmol) and phenyl-boronic acid (Aldrich, 91 mg. 0.75 mmol) according to the procedure of Example 3A (110 mg, yield. 69.3%). $^1$H NMR (300 MHz, CD$_3$OD) δ ppm 1.80-1.91 (m, 2 H), 1.91-1.99 (m, 2 H), 2.03-2.22 (m, 4 H), 3.17 (d, J=12.54 Hz, 1 H), 3.24-3.27 (m, 2 H), 3.28-3.29 (m, 2 H), 3.71 (d, J=12.54 Hz, 2 H), 6.82 (d, J=8.14 Hz, 1 H), 7.20-7.30 (m, 1 H), 7.32-7.41 (m, 3 H), 7.42-7.46 (m, 1 H), 7.48-7.56 (m, 2 H); MS (DCI/NH$_3$) m/z=318 (M+H)$^+$.

Example 10

3H-(4'r)-1'-Azaspiro[5-(indol-5-yl)-benzofuran-2,4']-tricyclo[3.3.1.1$^{3,7}$]decane Prepared from the product of Example 7A (160 mg 0.50 mmol) and indol-5-yl-boronic acid (Aldrich. 121 mg, 0.75 mmol) according to the procedure of Example 3A (170 mg, yield, 95.0%). $^1$H NMR (300 MHz, CD$_3$OD) δ ppm 2.05-2.27 (m, 7 H), 3.32-3.36 (m, 2 H), 3.43 (d, J=12.21 t Hz, 2 H), 3.47-3.54 (m, 2 H), 3.90 (d, J=12.54 Hz, 2 H), 6.45 (dd, J=3.05, 0.68 Hz, 1 H), 6.83 (d, J=8.48 Hz, 1 H), 7.23 (d, J=3.05 Hz, 1 H), 7.28 (dd, J=8.50, 1.70. Hz, 1 H), 7.34-7.42 (m, 2 H), 7.47 (d, J=1.36 Hz, 1 H), 7.66-7.69 (m, 1 H); MS (DCI/NH$_3$) m/z=357 (M+H)$^-$.

Example 11

3H-(4'r)-1'-Azaspiro[5-(benzo[b]thiophen-5-yl)-benzofuran-2,4']-tricyclo[3.3.1.1$^{3,7}$]decane Prepared from the product of Example 7A (160 mg 0.50 mmol) and 2-(1-benzothiophen-5-yl)-4,4,5,5-tetramethyl-1,3,2-dioxaborolane (Maybridge, 195 mg, 0.75 mmol) according to the procedure of Example 3A (140 mg, yield, 75.0%). $^1$H NMR (300 MHz, CD$_3$OD) δ ppm 2.10-2.21 (m, 7 H), 3.36-3.39 (m, 2 H), 3.44 (d, J=12.54 Hz, 2H). 3.47-3.53 (m, 2 H), 3.90 (d, J=11.87 Hz, 2 H), 6.88 (d, J=8.48 Hz. 11). 7.40 (d, J=5.42 Hz, 1 H), 7.45 (dd, J=8.48, 2.03 Hz, 1 H), 7.51-7.56 (m, 2 H), 7.57 (d, J=5.76 Hz. 1 H), 7.91 (cl. J=8.48 Hz. 1 H), 7.98 (d, J=1.36 Hz, 1 H); MS (DCI/NH$_3$) m/z=374 (M+H)$^+$.

Example 12

3H-(4'r)-1'-Azaspiro[5-(indol-4-yl)-benzofuran-2,4']-tricyclo[3.3.1.1$^{3,7}$]decane Prepared from the product of Example 7A (160 mg 0.50 mmol) and indol-4-yl boronic acid (Frontier, 121 mg, 0.75 mmol) according to the procedure of Example 3A (100 mg, yield, 56.0%). $^1$H NMR (300 MHz CD$_3$OD) δ ppm 2.04-2.46 (m, 7 H), 3.37-3.41 (m, 2 H), 3.43-3.59 (m, 4 H), 3.94 (d, J=12.21 Hz, 2 H), 6.55 (dd, J=3.22, 0.85 Hz, 1 H), 6.89 (d, J=8.14 Hz, 1 H), 6.99 (dd, J=7.40, 10.85 Hz, 1 H), 7.13 (dd, J=8.20, 7.40 Hz, 1 H), 7.25 (d, J=3.05 Hz, 1 H), 7.33 (dt, J=8.14, 1.02 Hz, 1 H), 7.44 (dd, J=8.31, 1.86 Hz, 1 H), 7.52 (d, J=1.36 Hz. 1 H); MS (DCI/NH$_3$) m/z=357 (M+H)$^+$.

Example 13

3H-(4'r)-1'-Azaspiro[5-(2-oxo-indolin-5-yl)-benzofuran-2,4']-tricyclo[3.3.1.1$^{3,7}$]decane Prepared from the product of Example 7A (160 mg 0.50 mmol) and 5-(4,4,5,5-tetramethyl-1,3,2-dioxaborolan-2-yl)indolin-2-one (ref. WO 2006065233, 194 mg, 0.75 mmol) according to the procedure of Example 3A (120 mg, yield, 64.4%). $^1$H NMR (300 MHz, CD$_3$OD) δ ppm 1.65-1.76 (m, 1 H), 1.79-1.87 (m, 2 H), 1.99-2.24 (m, 4 H), 3.05 (d, J=12.89 Hz, 2 H), 3.12-3.16 (m, 2 H), 3.23-3.26 (m, 2 H), 3.34 (s, 2 H), 3.62 (d, J=12.55 Hz, 2 H), 6.78 (d, J=8.14 Hz, 1 H), 6.91 (d, J=7.46 Hz. 1 H), 7.28 (dd, J=8.48, 2.03 Hz, 1 H), 7.37-7.40 (m, 2 H), 7.43 (d, J=1.36 Hz, 1 H); MS (DCI/NH$_3$) m/z=373 (M+H)$^+$.

Example 14

3H-(4'r)-1'-Azaspiro[5-(thiophen-3-yl)-benzofuran-2,4']-tricyclo[3.3.1.1$^{3,7}$]decane Prepared from the product of Example 7A (160 mg 0.50 mmol) and thiophen-3-yl boronic acid (Aldrich, 96 mg. 0.75 mmol) according to the procedure of Example 3A (160 mg, yield, 99.0%). $^1$H NMR (300 MHz, CD$_3$OD) δ ppm 2.05-2.40 (m, 7 H), 3.35 (s, 2 H), 3.49 (d, J=12.89 Hz, 2 H), 3.53-3.61 (m, 2 H), 3.92 (d, J=12.21 Hz, 2 H), 6.82 (d, J=8.48 Hz, 1 H), 7.36 (dd, J=5.10, 1.30 Hz, 1 H), 7.40-7.46 (m, 3 H) 7.51 (d, J=1.36 Hz, 1 H); MS (DCI/NH$_3$) m/z=324 (M+H)$^+$.

Example 15

3H-(4'r)-1'-Azaspiro[5-(1H-pyrrolo[2,3-b]pyridin-5-yl)-benzofuran-2,4']-tricyclo[3.3.1.1$^{3,7}$]decane

Example 15A 5-(4,4,5,5-Tetramethyl-1,3,2-dioxaborolan-2-yl)-1H-pyrrolo[2,3-b]pyridine 5-Bromo-1H-pyrrolo[2,3-b]pyridine (Alfa Aesar. 1.00 g, 5.0 mmol) was coupled with 4,4,4',4',5,5,5',5'-octamethyl-2,2'-bi(1,3,2-dioxaborolane) (Aldrich. 1.52 g, 6.0 mmol) under the catalysis of {1,1'-bis(diphenylphosphino)-ferrocene] dichloro-palladium(II) dichloromethane complex PdCl$_2$ (dppf).CH$_2$Cl$_2$ (Aldrich. 82 mg. 0.1 mmol) with KOAc (Aldrich, 0.98 g. 10.0 mmol) in dioxane (anhydrous, 20 mL) at 80° C. for 10 h. It was then cooled down to ambient temperature, concentrated and diluted with EtOAc (100 mL). The mixture was then washed with brine (2×10 mL). The organic solution was concentrated and the residue was purified chromatography (SiO$_2$. EtOAc/hexane, v. 50J50. R$_f$=0.40) to give the title compound (1.15 g, yield. 94.2%). $^1$H NMR (300 MHz, CD$_3$OD) δ ppm 1.38 (s, 12 H) 6.52 (d, J=3.39 Hz, 1 H) 7.38 (d, J=3.39 Hz, 1 H) 8.34 (d, J=1.70 Hz, 1 H) 8.49 (d, J=1.36 Hz, 1 H); MS (DCI/NH$_3$) m/z 245 (M+1)$^+$.

Example 15B 3H-(4'r)-1'-Azaspiro[5-(1H-pyrrol-[2,3-b]pyridin-5-yl)-benzofuran-2,4']-tricyclo[3.3.1.1$^{3,7}$]decane Prepared from the products of Example 7A (160 mg 0.50 mmol) and Example 15A (183 mg. 0.75 mmol) according to the procedure of Example 3A (150 mg, yield, 84.0%). $^1$H NMR (300 MHz. CD$_3$OD) δ ppm 2.10-2.31 (m, 7 H), 3.39 (s. 2 H), 3.48 (d, J=12.55 Hz, 2 H), 3.52-3.60 (m, 2 H), 3.94 (d, J=12.21 Hz, 2 H), 6.52 (d, J=3.73 Hz, 1 H). 6.90 (d, J=8.48 Hz, 1 H), 7.38-7.44 (m, 2 H), 7.51 (d, J=1.36 Hz, 11). 8.12 (d, J=2.03 Hz, 1 H), 8.35 (d, J=2.37 Hz, 1 H); MS (DCI/NH$_3$) m/z=358 (M+H)$^+$.

Example 16

3H-(4'r)-1'-Azaspiro[5-(thieno[2,3-b]pyridin-5-yl)-benzo[t]ran-2,4']-tricyclo[3.3.1.1$^{3,7}$]decane

Example 16A 1-(Thieno[2,3-b]pyridin-5-yl)ethanone

To a vigorously stirred mixture of 2-nitrothiophene (Aldrich, 12.9 g, 0.1 mol) in concentrated HCl (Aldrich, 36.5%, 195 mL) was carefully added tin (Aldrich, 100 mesh, 25 g, 0.21 mol) at 20-30° C. After most of tin metal had been dissolved, EtOH (Aldrich, 70 mL) and ZnCl$_2$ (Aldrich, 6.0 g, 0.044 mol) were added and the mixture was then heated to 75° C. for 1 h. The brown solution was cooled down to ambient temperature and 4,4-dimethoxybutan-2-one (Aldrich, 39.6 g, 0.3 mol) in EtOH (50 mL) was added. The reaction mixture was stirred at 70° C. for 10 h. The cooled brown reaction mixture was poured into NaOH aqueous solution (50%. 160 mL) and extrated with EtOAc (3×500 mL). The combined extracts were washed with brine (2×50 mL) and concentrated. The residue was purified with chromatography (SiO$_2$, EtOAc/hexane, v. 20/80, R$^f$=0.30) to give the title compound (4.20 g, yield, 23%). $^1$H NMR (300 MHz, CDCl$_3$) δ ppm 2.72 (s, 3 H), 7.38 (d, J=6.10 Hz, 1 H), 7.64 (d, J=6.10 Hz, 1 H), 8.63 (d, J=2.03 Hz, 1 H), 9.14 (d, J=2.03 Hz, 1 H); MS (DCI/NH$_3$) M/z 178 (M+1)$^+$, 195 (M+NH$_4$).

Example 16B 1-(Thieno[2,3-b]pyridin-5-yl)ethanone oxime

The product of Example 16A (3.89 g, 22 mmol) was treated with NH$_2$OH.H$_2$O (Aldrich, 1.35 g, 26.4 mmol) in pyridine (30 mL) and EtOH (30 mL) at 80° for 3 h. It was cooled down to ambient temperature and concentrated under reduced pressure. The residue was recrystallized with EtOH (Aldrich, 90%) to give the title compound (3.86 g, yield. 91.4%) $^1$H NMR (300 MHz. CDCl$_3$) δ ppm 2.37 (s, 3 H), 7.30 (d, J=5.76 Hz. 1 H), 7.56 (d, J=5.76 Hz. 1 H), 7.70 [s(broad.), 1H], 8.28 (d, J=2.03 Hz, 1 H), 8.90 (d, J=2.37 Hz, 1 H); MS (DCI/NH$_3$) m/z 193 (M+1)$^+$. 210 (M+NH$_4$)$^+$.

Example 16C

N-(Thieno[2,3-b]pyridin-5-yl)acetamide

The product of Example 16B (3.84 g, 20 mmol) was treated with PCl$_5$ (Aldrich. 6.26 g. 30 mmol) in benzene (Aldrich, anhydrous, 100 mL) at 80° for 1 h. It was then cooled down to ambient temperature and poured into ice (100 g). After being basified with NaOH (Aldrich, 50%) till pH=9-100 the reaction mixture was extracted with EtOAc (3×200 mL). The combined extracts were washed with brine (2×50 mL) and concentrated. The residue was purified with chromatography (SiO$_2$. EtOAc/hexane, v. 50/50, R$^f$=0.40) to give the title compound (2.10 g. yield. 54.7%). $^1$H NMR (300 MHz, CDCl$_3$) δ ppm 2.26 (s, 3 H), 7.24 (s, 1 H), 7.56 (d, J=6.10 Hz, 1 H), 8.45 (d, J=2.03 Hz, 1 H). 8.69 (d, J=2.03 Hz, 1 H); MS (DCI/NH$_3$) m/z 193 (M+1)$^+$.

Example 16D

Thieno[2,3-b]pyridin-5-amine

The product of Example 16C (1.92 g. 10 mmol) was treated with concentrated HCl (Aldrich, 30 mL) at 800 f for 14 h. It was then cooled down to ambient temperature and the pH adjusted with NaOH (Aldrich, 50%) base until pH=8-9. The reaction mixture was extracted with CHCl$_3$ (3×100 mL). The combined extracts were washed with brine (2×30 mL) and concentrated to give the title compound (1.38 g, yield, 92.0%). $^1$H NMR (300 MHz. CD$_3$OD) δ ppm 7.13 (d, J=5.76 Hz, 1 H), 7.47 (d, J=2.71 Hz, 1 H), 7.56 (d, J=5.76 Hz, 1 H), 8.07 (d, J=2.37 Hz, 1 H); MS (DCI/NH$_3$) m/z 151 (M+1).

Example 16E

5-Bromothieno[2,3-b]pyridine

The product of Example 16D (1.35 g. 9.0 mmol) was treated with iso-amylnitrite (Aldrich. 2.10 g. 18.0 mmol) and CuBr$_2$ (Aldrich, 4.03 g. 18.0 mmol) in MeCN (20 mL) at ambient temperature overnight. The reaction mixture was quenched with saturated NH$_4$Cl (20 mL) and then extracted with EtOAc (3×50 mL). The combined extracts were washed with brine (2×30 mL) and concentrated. The residue was purified with chromatography (SiO$_2$, EtOAc/hexane, v. 80/20. R$^f$=0.80) to give the title compound (1.03 g, yield, 53.0%). $^1$H NMR (300 MHz, CDCl$_3$) δ ppm 7.22 (d, J=6.10 Hz, 1 H), 7.58 (d, J=6.10 Hz, 1 H), 8.21 (d, J=2.37 Hz, 1 H), 8.61 (d, J=2.0(3 Hz, 1 H);MS (DCI/NH$_3$) m/z 214 (M+1)$^+$, 216 (M+1)$^+$.

Example 16F 5-(4,4,5,5-Tetramethyl-1,3,2-dioxaborolan-2-yl)thieno[2,3-b]pyridine The title compound was prepared from the product of Example 16E (1.00 g, 7.4 mmol) and 4,4,4',4',5,5,5',5'-octamethyl-2,2'-bi(1,3,2-dioxahorolanie) (Aldrich, 1.43 g, 5.64 mmol) according to the procedure of Example 15A (1.22 g, yield, 99%). $^1$H NMR (300 MHz, CD$_3$OD) δ ppm 1.39 (s, 12 H), 7.42 (d, J=6.10 Hz, 1 H), 7.72 (d, J=5.76 Hz, 1 H), 8.55 (d, J=1.36 Hz, 1 H), 8.76 (d, J=1.70 Hz, 1 H); MS (DCI/NH$_3$) m/z 261 (M+1)$^+$.

Example 16G 3H-(4r)-1'-Azaspiro[5-(thieno[2,3-b]pyridin-5-yl)-benzofuran-2,4']-tricyclo[3.3.1.1$^{3,7}$]decane The title compound was prepared from the product of Example 7A (160 mg 0.50 mmol) and Example 16F (196 mg, 0.75 mmol) according to the procedure of Example 3A (80 mg, yield. 42.7%). $^1$H NMR (300 MHz, CD$_3$OD) δ ppm 1.65-1.80 (m, 1 H), 1.83-1.92 (m, 2 H), 2.00-2.26 (m, 4 H), 3.00-3.19 (m, 4 H), 3.34 (s, 2 H), 3.63 (d, J=12.88 Hz. 2 H), 6.89 (d, J=8.48 Hz, 1 H), 7.41 (d, J=6.10 Hz, 1 H), 7.46 (dd, J=8.48, 2.03 Hz, 1 H). 7.55 (d, J=1.70 Hz, 1 H), 7.74 (d, J=5.76 Hz, 1 H), 8.38 (d, J=2.03 Hz, 1 H), 8.71 (d, J=2.37 Hz, 1 H): MS (DCI/NH$_3$) m/z=375 (M+H)$^-$.

Compositions of the Invention

The invention also provides pharmaceutical compositions comprising a therapeutically effective amount of a compound of formula (I) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral injection or for rectal administration.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose, and sucrose; starches such as corn starch and potato starch; cellulose and its derivatives, such as sodium carboxymethyl cellulose, ethyl cellulose, and cellulose acetate; powdered tragacanth; malt; gelatin; talc; cocoa butter; suppository waxes; oils such as peanut oil, cottonseed oil, safflower oil, sesame oil, olive oil, corn oil, and soybean oil: glycols; such a propylene glycol; esters such as ethyl oleate and ethyl laurate: agar; buffering agents such as magnesium hydroxide and aluminum hydroxide: alginic acid; pyrogen-free water; isotonic saline: Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives, and antioxidants can also be present in the composition, according to the judgment of one skilled in the art of formulations.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration, including intravenous, intramuscular, intraperitoneal, intrasternal, subcutaneous, intraarticular injection, and infusion.

Pharmaceutical compositions for parenteral injection comprise pharmaceutically acceptable sterile aqueous or non-aqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions can also contain adjuvants such as preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. It also can be desirable to include isotonic agents, for example, sugars, sodium chloride and the like. Prolonged absorption of the injectable pharmaceutical form can be brought about by the use of agents delaying absorption, for example, aluminum monostearate and gelatin.

In some cases, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug can depend upon its rate of dissolution, which, in turn, may depend upon crystal size and crystalline form. Alternatively, a parenterally administered drug form can be administered by dissolving or suspending the drug in an oil vehicle.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions can be formulated according to the known art using suitable dispersing or wetting agents and suspending agents. The sterile injectable preparation also can be a sterile injectable solution, suspension or emulsion in a nontoxic, parenterally acceptable diluent or solvent such as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate in addition to or alternatively with only, a) fillers or extenders such as starches, lactose, sucrose, glucose, mannitol, and salicylic acid: b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin: f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well-known in the pharmaceutical formulating art. They can optionally contain opacifying agents and can also be of a composition that they release the active ingredient(s) only, or preferentially, in a certain part of the intestinal tract in a delayed manner. Examples of materials useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants, or patches. A desired compound of the invention is admixed under sterile conditions with a pharmaceutically acceptable carrier and any needed preservatives or buffers as may be required. Ophthalmic formulation, eardrops, eye ointments, powders, and solutions are also contemplated as being within the scope of this invention.

The ointments, pastes, creams and gels may contain, in addition to an active compound of this inventions animal fats, vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention also can be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art, See, for example, Prescott, Ed., Methods in Cell Biology, Volume XIV, Academic Press. New York. N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants. Ophthalmic formulations, eye ointments, powders and solutions are also contemplated as being within the scope of this invention. Aqueous liquid compositions of the invention also are particularly useful.

The compounds of the invention can be used in the form of pharmaceutically acceptable salts, esters, or amides derived from inorganic or organic acids. The term "pharmaceutically acceptable salts, esters and amides," as used herein, include salts, zwitterions, esters and amides of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid.

Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate, and undecanoate.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides, and iodides: arylalkyl halides such as benzyl and phenethyl bromides, and others. Water or oil-soluble or dispersible products are thereby obtained.

Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid, and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine diethylamine, ethylamine and the such as. Other representative organic amines useful for the formation of base addition salts include ethylenediamine, ethanolamine, diethanolamine, piperidine, and piperazine.

The term "pharmaceutically acceptable ester," as used herein, refers to esters of compounds of the invention which hydrolyze in vivo and include those that break down readily in the human body to leave the parent compound or a salt thereof. Examples of pharmaceutically acceptable, non-toxic esters of the invention include $C_1$-to-$C_6$ alkyl esters and $C_5$-to-$C_7$ cycloalkyl esters, although $C_1$-to-$C_4$ alkyl esters are preferred. Esters of the compounds of formula (I) can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, alkyl triflate, for example with methyl iodide, benzyl iodide, cyclopentyl iodide. They also can be prepared by reaction of the compound with an acid such as hydrochloric acid and an alkylcarboxylic acid such as acetic acid, or with acid and an arylcarboxylic acid such as benzoic acid.

The term "pharmaceutically acceptable amide," as used herein, refers to non-toxic amides of the invention derived from ammonia, primary $C_1$-to-$C_6$ alkyl amines and secondary $C_1$-to-$C_6$ dialkyl amines. In the case of secondary amines, the amine can also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula (I) can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also can be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the invention in the form of a pharmaceutically acceptable prodrug.

The term "pharmaceutically acceptable prodrug" or "prodrug," as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of formula (I), for example, by hydrolysis in blood. A thorough discussion is provided in T. Higuchi and V. Stella, Pro-drugs as Novel Delivery Systems. V. 14 of the A.C.S. Symposium Series, and in Edward B. Roche, ed., Bioreversible Carriers in Drug Design. American Pharmaceutical Association and Pergamon Press (1987).

The invention also contemplates pharmaceutically acceptable compounds that when administered to a patient in need may be converted through in vivo biotransformation into compounds of formula (I).

Determination of Biological Activity

To determine the effectiveness of representative compounds of this invention as α7 nAChRs, the compounds of the invention were evaluated according to the [$^3$H]-methyllycaconitine (MLA) binding assay, or the [$^3$H]-DPPB binding assay, and considering the [$^3$H]-cytisine binding assay, which were performed as described below.

[$^3$H]-Cytisine Binding

Binding conditions were modified from the procedures described in Pabreza L A, Dhawan, S, Kellar K J, [$^3$H]-Cytisine Binding to Nicotinic Cholinergic Receptors in Brain, Mol. Pharm. 39: 9-12, 1991. Membrane enriched fractions from rat brain minus cerebellum (ABS Inc., Wilmington, Del.) were slowly thawed at 4° C., washed and resuspended in 30 volumes of BSS-Tris buffer (120 mM NaCl/5 mM KCl/2 mM $CaCl_2$/2 mM $MgCl_2$/50 mM Tris-Cl, pH 7.4, 4° C.). Samples containing 100-200 µg of protein and 0.75 nM [$^3$H]-cytisine (30 $C_i$/mmol; Perkin Elmer/NEN Life Science Products, Boston, Mass.) were incubated in a final volume of 500 µL for 75 minutes at 4° C. Seven log-dilution concentrations of each compound were tested in duplicate. Non-specific binding was determined in the presence of 10 µM (−)-nicotine. Bound radioactivity was isolated by vacuum filtration onto prewetted glass fiber filter plates (Millipore, Bedford, Mass.) using a 96-well filtration apparatus (Packard Instruments, Meriden. Conn.) and were then rapidly rinsed with 2 mL of ice-cold BSS buffer (120 mM NaCl/5 mM KCl/2 mM $CaCl_2$/2 mM $MgCl_2$). Packard MicroScint-20® scintillation cocktail (40 µL) was added to each well and radioactivity determined using a Packard TopCount® instrument. The $IC_{50}$ values were determined by nonlinear regression in Microsoft Excel® software. $K_i$ values were calculated from the $IC_{50}$s using the Cheng-Prusoff equation, where $K_i=IC_{50}/(1+[Ligand]/K_D)$.

[$^3$H]-Methyllycaconitine (MLA) Binding

Binding conditions were similar to those for [3H]-cytisine binding. Membrane enriched fractions from rat brain minus cerebellum (ABS Inc., Wilmington, Del.) were slowly thawed at 4° C., washed and resuspended in 30 volumes of BSS-Tris buffer (120 mM NaCl, 5 mM KCl, 2 mM $CaCl_2$. 2 mM $MgCl_2$, and 50 mM Tris-Cl. pH 7.4, 22° C.). Samples containing 100-200 µg of protein, 5 nM [3H]-MLA (25 $C_i$/mmol; Perkin Elmer/NEN Life Science Products. Boston. MA) and 0.1% bovine serum albumin (BSA, Millipore. Bedford, Mass.) were incubated in a final volume of 500 µL for 60 minutes at 22° C. Seven log-dilution concentrations of each compound were tested in duplicate. Non-specific binding was determined in the presence of 10 ™ MLA. Bound radioactivity was isolated by vacuum filtration onto glass fiber filter plates prewetted with 2% BSA using a 96-well filtration apparatus (Packard Instruments, Meriden, Conn.) and were then rapidly rinsed with 2 mL of ice-cold BSS. Packard MicroScint-20® scintillation cocktail (40 µL) was added to each well and radioactivity was determined using a Packard TopCount® instrument. The $IC_{50}$ values were determined by nonlinear regression in Microsoft Excel® software. $K_i$ values were calculated from the $IC_{50}$S using the Cheng-Prusoff equation, where $K_i=IC_{50}/(I+[Ligand]/K_D)$.

[$^3$H]-DPPB Binding

[$^3$H]-DPPB. [$^3$H]-(S,S)-2,2-dimethyl-5-(6-phenyl-pyridazin-3-yl)-5-aza-2-azonia-bicyclo[2.2.1]heptane iodide, binding to the α7 nAChR subtype was determined using membrane enriched fractions from rat brain minus cerebellum or human cortex (ABS Inc., Wilmington, Del.). Pellets were thawed at 4° C., washed and resuspended with a Polytron at a setting of 7 in 30 volumes of BSS-Tris buffer (120 mM NaCl, 5 mM KCl, 2 mM $CaCl_2$, 2 mM $MgCl_2$, and 50 mM Tris-Cl. pH 7.4, 4° C.). Seven log-dilution concentrations of test compounds containing 100-200 µg of protein. and 0.5 nM [$^3$H]-DPPB (62.8 Ci/mmol; R46V. Abbott Labs) were incubated in a final volume of 500 µl for 75 minutes at 4° C. in duplicate. Non-specific binding was determined in the presence of 10 µM methyllycaconitine. Bound radioactivity was collected on Millipore MultiScreen® harvest plates FB presoaked with 0.3% PEI using a Packard cell harvester, washed with 2.5 ml ice-cold buffer, and radioactivity was determined using a Packard TopCount Microplate beta counter. $IC_{50}$ values were determined by nonlinear regression in Microsoft® (Excel or Assay Explorer). $K_i$ values were calculated from the $IC_{50}$s using the Cheng-Prusoff equation, where $K_i=IC_{50}i(1+[Ligand]/K_D)$. [$^3$H]-DPPB was obtained according to the preparation procedures described below.

[Methyl-1H]2,2-Dimethyl-5-(6-phenyl-pyridazin-3-yl)-5-aza-2-azonia-bicyclo[2.2.1]heptane; iodide Preparation

[Methyl-3H]2,2-dimethyl-5-(6-phenyl-pyridazin-3-yl)-5-aza-2-azonia-bicyclo[2.2.1]heptane; iodide used in the [$^3$H]-DPPB binding assay above was prepared according to the following procedures.

Step 1

Preparation of t-Butyl (S,S)-5-(6-Phenyl-pyridazin-3-yl)-2,5-diaza-bicyclo[2.2.1]heptane-2-carboxylate Triethylamine (20 mL) was added to a suspension of t-butyl (S,S)-2,5-diazabicyclo[2.2.1]heptane-2-carboxylate (3.43 g, 17.3 mmol, Aldrich Chemical Company) and 3-chloro-6-phenylpyridazine (3.30 g. 17.3 mmol, Aldrich Chemical Company) in toluene (50 mL) and the mixture was heated under nitrogen at 100° C. for 7 days. The dark mixture was cooled to room temperature, and the resulting precipitate was isolated by filtration, washed with toluene (15 mL) and dried under vacuum to provide the title compound as an off-white solid (3.00 g). The filtrate was concentrated and the residue was purified by column chromatography on silica gel, eluting with ethyl acetate, to provide additional product (0.41 g, total yield 3.41 g, 56%); MS (DCI/NH$_3$) m/z 353 (M+H)$^+$.

Step 2

Preparation of (S,S)-2-Methyl 5-(6-phenyl-pyridazin-3-yl)-2,5-diaza-bicyclo[2.2.1]heptane The product obtained from Step 1 (3.41 g. 9.7 mmol) was dissolved in formic acid (20 mL) and treated with formalin (37% by weight. 1.0 g. 12.3 mmol). The mixture was heated at 100° C. for 1 h, and the brown solution was cooled to room temperature and concentrated under vacuum. The residue was purified by column chromatography on silica gel, eluting with CH$_2$Cl, —CH$_3$OH—NH$_4$OH (95:5:1) to provide the title compound as an off-white solid (2.50 g, 96%); MS (DCI/NH$_3$) m/z 267 (M+H)$^+$.

Step 3

Preparation of [$^3$H]-(S,S)-2,2-Dimethyl-5-(6-phenyl-pyridazin-3-yl)-5-aza-2-azonia-bicyclo[2.2.1]heptane iodide ([$^3$H]-DPPB)

[$^3$H]Methyl iodide in toluene (250 mCi in 0.1 mL, 85Ci/mmol, American Radiolabeled Chemicals, Inc.) was combined with a solution of the product obtained from Step 2 in dichloromethane (0.788 mg, 2.96 µmole in 0.45 mL). The vial was capped and the mixture was allowed to react overnight at room temperature. Methanol was added and the solvents were evaporated to give 42 mCi. The product was taken up in methanol for HPLC purification.

Step 4

Purification by High Performance Liquid Chromatography (HPLC)

About 7 mCi of [$^3$H]-DPPB was evaporated to dryness and the residue was dissolved in total about 4.5 ml acetonitrile:water:TFA (15:85:0.1). Approximately 0.9 mL per injection were made onto a Phenomenex Luna C18(2) column (5 micron, 250 mm×4.6 mm ID) using an Agilent HPLC system. [$^3$H]-DPPB was eluted by a gradient mobile phase from 10% B to 20% B in 20 min where Mobile Phase A=0.1% trifluoroacetic acid in water and Mobile Phase B=0.1% trifluoroacetic acid in acetonitrile at a flow rate of approximately 1 in mL/min. Peak detection and chromatograms were obtained with an Agilent variable wavelength UV detector set at 275 nm. The fractions containing [$^3$H]-DPPB were collected at approximately 14 minutes using an Agilent fraction collector. The fractions were combined and the solvents were evaporated in vacuo. The residue was dissolved in 200 proof ethanol (2 mL) to give 0.7 mCi.

Step 5

Determination of Purity and Specific Activity

[$^3$H]-DPPB was assayed using an Agilent 1100 series HPLC system consisting of a quaternary pump, an autosampler, and a photodiode array UV detector. A Packard Radiomatic A 500 radioactivity detector was connected to the HPLC system. For radiodetection, a 500 µL flow cell and a 3:1 ratio of Ultima-Flo M scintillation cocktail to HPLC mobile phase were used. The analyses were performed using a Phenomenex Luna C18(2) column (5 microns. 250 mm×4.6 mm ID). The mobile phase consisted of a gradient starting with 10% B and ramping to 20% B in 20 minutes followed by ramping to 90% B in 1 minute and hold at 90% B for 9 minutes, where Mobile Phase A=0.1% trifluoroacetic acid in water and Mobile Phase B=0.1% trifluoroacetic acid in acetonitrile. The flow rate was set at approximately 1 mL/min and the UV detection was set at 275 nm.

Compounds of the invention had K$_i$ values of from about 1 nanomolar to about 10 micromolar when tested by the [$^3$H]-MLA assay, many having a K$_i$ of less than 1 micromolar. [$^3$H]-Cytisine binding values of compounds of the invention ranged from about 50 nanomolar to at least 100 micromolar. Preferred compounds typically exhibited greater potency at α7 receptors compared to α4β2 receptors. The determination of preferred compounds typically considered the K$_i$ value as measured by MLA assay in view of the K$_i$ value as measured by [$^3$H]-cytisine binding, such that in the formula D= K$_{i\ H\text{-cytisine}}^3$/K$_{i\ MLA}$. D is greater than about 50. Alternatively, the K$_i$ value as measured by [$^3$H]-DPPB assay can be used in place of the K$_{i\ MLA}$ such that in the formula D'=K$_{i\ H\text{-cytisine}}^3$/K$_{i[3H]\text{-}DPPB}$. D' is greater than about 50.

Compounds of the invention are α7 nAChRs ligands that modulate function of α7 nAChRs by altering the activity of the receptor or signaling. The compounds can be inverse agonists that inhibit the basal activity of the receptor or antagonists that completely block the action of receptor-activating agonists. The compounds also can be partial agonists that partially block or partially activate the α7 nAChR receptor or agonists that activate the receptor. Binding to α7 receptor also trigger key signaling processes involving various kinases and phosphatases and protein-protein interactions that are important to effects on memory, cytoprotection, gene transcription and disease modification.

Methods of the Invention

Compounds and compositions of the invention are useful for modulating the effects of nAChRs, and more particularly α7 nAChRs. In particular, the compounds and compositions of the invention can be used for treating and preventing disorders modulated by α7 nAChRs5. Typically, such disorders can be ameliorated by selectively modulating the α7 nAChRs in a mammal, preferably by administering a compound or composition of the invention, either alone or in combination with another active agent, for example, as part of a therapeutic regimen. Also, some compounds of the invention possess affinity at the α4β2 nAChRs in addition to α7 nAChRs, and selective compounds with dual affinities at both receptor subtypes also are expected to have beneficial effects.

The compounds of the invention, including but not limited to those specified in the examples, possess an affinity for nAChRs, and more particularly α7 nAChRs. As α7 nAChRs ligands, the compounds of the invention can be useful for the treatment and prevention of a number of α7 nAChR-mediated diseases or conditions.

For example, α7 nAChRs have been shown to play a significant role in enhancing cognitive function, including aspects of learning, memory and attention (Levin, E. D., J. Neurobiol. 53: 633-640, 2002). As such, α7 ligands are suitable for the treatment of cognitive disorders including, for example, attention deficit disorder, attention deficit hyperactivity disorder (ADHD), Alzheimer-'s disease (AD), mild cognitive impairment, senile dementia. AIDS dementia. Pick's Disease, dementia associated with Lewy bodies, and dementia associated with Down's syndrome, as well as cognitive deficits associated with schizophrenia.

In addition, α7-containing nAChRs have been shown to be involved in the neuroprotective effects of nicotine both in vitro (Jonnala. R. B. and Buccafusco. J. J., J. Neurosci. Res. 66: 565-572, 2001) and in vivo (Shimohama, S. et al., Brain Res. 779: 359-363, 1998). More particularly, neurodegeneration underlies several progressive CNS disorders, including, but not limited to. Alzheimer's disease, Parkinson's disease, amyotrophic lateral sclerosis, Huntington's disease, dementia with Lewy bodies, as well as diminished CNS function resulting from traumatic brain injury. For example, the impaired function of α7 nAChR by β-amyloid peptides linked to Alzheimer's disease has been implicated as a key factor in development of the cognitive deficits associated with the disease (Liu, Q.-S., Kawai, H. Berg, D. K., PNAS 98: 4734-4739, 2001). The activation of α7 nAChRs has been shown to block this neurotoxicity (Kihara, T. et al., J. Biol. Chem. 276: 13541-13546, 2001). As such, selective ligands that enhance 0:7 activity can counter the deficits of Alzheimer's and other neurodegenerative diseases.

Schizophrenia is a complex disease that is characterized by abnormalities in perception, cognition, and emotions. Significant evidence implicates the involvement of α7 nAChRs in this disease, including a measured deficit of these receptors in post-mortem patients (Leonard, S. Eur. J. Pharmacol. 393: 237-242, 2000). Deficits in sensory processing (gating) are one of the hallmarks of schizophrenia. These deficits can be normalized by nicotinic ligands that operate at the α7 nAChR (Adler L. E. et al., Schizophrenia Bull. 24: 189-202, 1998; Stevens, K. E. et al., Psychopharmacology 136: 320-327, 1998). Thus, α7 ligands demonstrate potential in the treatment schizophrenia.

Angiogenesis, a process involved in the growth of new blood vessels, is important in beneficial systemic functions, such as wound healing, vascularization of skill grafts, and enhancement of circulation, for example, increased circulation around a vascular occlusion. Non-selective nAChR agonists like nicotine have been shown to stimulate angiogenesis (Heeschen. C. et al., Nature Medicine 7: 833-839, 2001). Improved angiogenesis has been shown to involve activation of the α7 nAChR (Heeschen, C. et al. J. Clin. Invest. 110: 527-536, 2002). Therefore, nAChR ligands that are selective for the α7 subtype offer improved potential for stimulating angiogenesis with an improved side effect profile.

A population of α7 nAChRs in the spinal cord modulate serotonergic transmission that have been associated with the pain-relieving effects of nicotinic compounds (Cordero-Erausquin. M. and Changeux. J.-P. PNAS 98:2803-2807, 2001). The α7 nAChR ligands demonstrate therapeutic potential for the treatment of pain states, including acute pain, post-surgical pain, as well as chronic pain states including inflammatory pain and neuropathic pain. Moreover. α7 nAChRs are expressed on the surface of primary macrophages that are involved in the inflammation response, and that activation of the α7 receptor inhibits release of TNF and other cytokines that trigger the inflammation response (Wang. H. et al Nature 421: 384-388, 2003). Therefore, selective α7 ligands demonstrate potential for treating conditions involving TNF-mediated diseases, for example, rheumatoid arthritis, Crohn's disease, ulcerative colitis, inflammatory bowel disease, organ transplant rejection, acute immune disease associated with organ transplantation, chronic immune disease associated with organ transplantation, septic shock, toxic shock syndrome, sepsis syndrome, depression, and rheumatoid spondylitis.

The mammalian sperm acrosome reaction is an exocytosis process important in fertilization of the ovum by sperm. Activation of an α7 nAChR on the sperm cell has been shown to be essential for the acrosome reaction (Son, J.-H. and Meizet, S. Biol. Reproduct. 68: 1348-1353 2003). Consequently, selective α7 agents demonstrate utility for treating fertility disorders.

Compounds of the invention are particularly useful for treating and preventing a condition or disorder affecting cognition, neurodegeneration, and schizophrenia.

Cognitive impairment associated with schizophrenia often limits the ability of patients to function normally, a symptom not adequately treated by commonly available treatments, for example, treatment with an atypical antipsychotic. (Rowley, M. et al. J. Med. Chem. 44: 477-501, 2001). Such cognitive deficit has been linked to dysfunction of the nicotinic cholinergic system, in particular with decreased activity at (α7 receptors. (Friedman, J. I. et al. Biol Psychiatry. 51: 349-357, 2002). Thus, activators of α7 receptors can provide useful treatment for enhancing cognitive function in schizophrenic patients who are being treated with atypical antipsychotics. Accordingly, the combination of an α7 nAChR ligand and an atypical antipsychotic would offer improved therapeutic utility. Specific examples of suitable atypical antipsychotics include, but are not limited to clozapine, risperidone olanzapine, quietapine, ziprasidone, zotepine, iloperidone, and the like.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salt, ester, amide or prodrug form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed: and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal range from about 0.010 mg/kg body weight to about 1 g/kg body weight. More preferable doses can be in the range of from about 0.010 mg/kg body weight to about 100 mg/kg body weight. If desired, the effective daily dose can be divided into multiple doses for purposes of administration. Consequently, single dose compositions may contain such amounts or submultiples thereof to make up the daily dose.

Compounds of the invention are α7 nAChRs ligands that modulate function of α7 nAChRs by altering the activity of the receptor or signaling. The compounds can be inverse agonists that inhibit the basal activity of the receptor or antagonists that completely block the action of receptor-activating agonists. The compounds also can be partial agonists that partially block or partially activate the α7 nAChR receptor or agonists that activate the receptor. Binding to α7 receptor also trigger key signaling processes involving various kinases and phosphatases and protein-protein interactions that are important to effects on memory cytoprotection, gene transcription and disease modification. Therefore, the administration of a therapeutically effective amount of a compound of formula (I) to a mammal provides a method of selectively modulating the effects of α4β2, α7, or both α4β2 and α7 nicotinic acetylcholine receptors.

Furthermore, the administration of a therapeutically effective amount of a compound of formula (I) to a mammal provides a method of treating or preventing a condition or disorder selected from the group consisting of attention deficit disorder, attention deficit hyperactivity disorder (ADHD). Alzheimer's disease (AD), mild cognitive impairment, senile dementia. AIDS dementia, Pick's Disease, dementia associated with Lewy bodies, dementia associated with Down's syndrome, amyotrophic lateral sclerosis, Huntington's disease, diminished CNS function associated with traumatic brain injury, acute pain, post-surgical pain, chronic pain, inflammatory pain, neuropathic pain, infertility, need for new blood vessel growth associated with wound healing, need for new blood vessel growth associated with vascularization of skin grafts, and lack of circulation more particularly circulation around a vascular occlusion, rheumatoid arthritis, Crohn's disease, ulcerative colitis, inflammatory bowel disease, organ transplant rejection, acute immune disease associated with organ transplantation, chronic immune disease associated with organ transplantation, septic shock, toxic shock syndrome, sepsis syndrome, depression, and rheumatoid spondylitis. More preferred, the administration of a therapeutically effective amount of a compound of formula (I) to a mammal provides a method of treating cognitive disorders, neurodegeneration, and schizophrenia. Furthermore, compounds of formula (I) may also be administered in combination with an atypical antipsychotic.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A compound of formula (I)

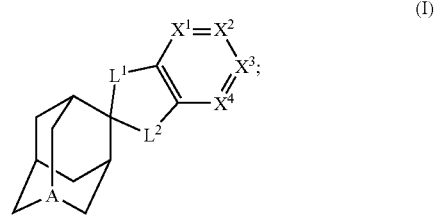

or a pharmaceutically acceptable salt or prodrug thereof, wherein

A is N;
$X^1$ is $CR^{x1}$;
$X^2$ is $CR^{x2}$;
$X^3$ is $CR^{x3}$;
$X^4$ is $CR^{x4}$;
$L^1$ is —O—;
$L^2$ is —CH$_2$—; and
$R^{x1}$, $R^{x2}$, $R^{x3}$, and $R^{x4}$ are each independently H, alkyl, aryl, halogen, or heteroaryl.

2. The compound according to claim 1, wherein at least one $R^{x1}$, $R^{x2}$, $R^{x3}$, and $R^{x4}$ is

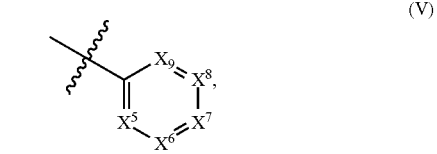

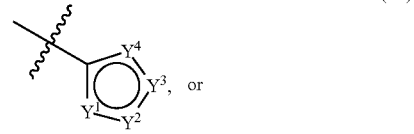

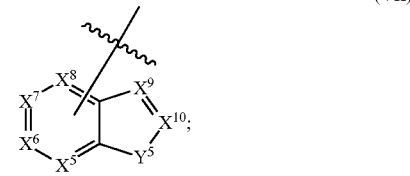

wherein
X$^5$ is CR$^{x5}$ or N;
X$^6$ is CR$^{x6}$ or N;
X$^7$ is CR$^{x7}$ or N;
X$^8$ is CR$^{x8}$ or N;
X$^9$ is CR$^{x9}$ or N;
X$^{10}$ is CR$^{x10}$ or N;
Y$_1$ is CR$^{y1}$, N; O, or S;
Y$_2$ is CR$^{y2}$, N; O, or S;
Y$_3$ is CR$^{y3}$, N; O, or S;
Y$_4$ is CR$^{y4}$, N; O, or S;
Y$_5$ is CR$^{y5}$, N; O, or S;
R$^{x5}$, R$^{x6}$, R$^{x7}$, R$^{x8}$, and R$^{x9}$, and R$^{x10}$ are each independently H, alkyl, aryl, cycloalkyl, halogen, halo alkyl, heteroaryl, OR$^b$, NR$^d$R$^e$, COR$^b$, CN, CO$_2$R$^b$, or CONR$^d$R$^e$;
R$^{y1}$, R$^{y2}$, R$^{y3}$ and R$_{y4}$ are each independently H, alkyl, aryl, cycloalkyl, halogen, halo alkyl, heteroaryl, OR$^b$, NR$^d$R$^e$, COR$^b$, CN, CO$_2$R$^b$, or CONR$^d$R$^e$;
R$^{y5}$ is H, alkyl, aryl, alkylcarbonyl, alkoxycarbonyl, or heteroaryl; and
R$^b$, R$^d$, and R$^e$ are independently H, alkyl, aryl, alkylcarbonyl, alkoxycarbonyl, or heteroaryl.

3. The compound according to claim 2, wherein, one of R$^{x2}$ or R$^{x3}$ is

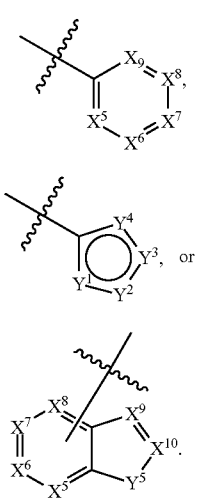

(V)

(VI)

(VII)

4. The compound according to claim 3, wherein one of R$^{x2}$ or R$^{x3}$ is

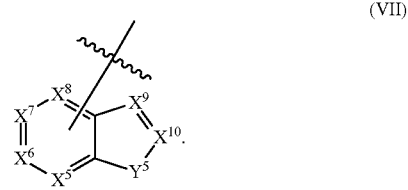

(VII)

5. The compound according to claim 4, wherein R$^b$ is H.
6. A compound of claim 1, wherein the compound is
3H-(4's)-1'-azaspiro[benzofuran-2,4']-tricyclo[3.3.1.1$^{3,7}$]decane;
3H-(4's)-1'-azaspiro[5-bromobenzofuran-2,4']-tricyclo[3.3.1.1$^{3,7}$]decane;
3H-(4's)-1'-azaspiro[5-phenylbenzofuran-2,4']-tricyclo[3.3.1.1$^{3,7}$]decane;
3H-(4's)-1'-azaspiro[5-(indol-5-yl)-benzofuran-2,4]'-tricyclo[3.3.1.1$^{3,7}$]decane;
3H-(4's)-1'azaspiro[5-(indol-6-yl)-benzofuran-2,4']-tricyclo[3.3.1.1$^{3,7}$]decane;
3H-(4's)-1'azaspiro[5-(indol-4-yl)-benzofuran-2,4']-tricyclo[3.3.1.1$^{3,7}$]decane;
3H-(4'r)-1'-azaspiro[benzofuran-2,4']-tricyclo[3.3.1.1$^{3,7}$]decane;
3H-1-(4'r)-1'-azaspiro[5-bromobenzofuran-2,4']-tricyclo[3.3.1.1$^{3,7}$]decane;
3H-(4'r)-1'-azaspiro[5-phenylbenzofuran-2,4']-tricyclo[3.3.1.1$^{3,7}$]decane;
3H-(4'r)-1'-azaspiro[5-(indol-5-yl)-benzofuran-2,4']-tricyclo[3.3.1.1$^{3,7}$]decane;
3H-(4'r)-1'-azaspiro[5-(benzo[b]thiophen-5-yl)-benzofuran-2,4']-tricyclo[3.3.1.1$^{3,7}$]decane;
3H-(4'r)-1'-azaspiro[5-(indol-4-yl)-benzofuran-2,4']-tricyclo[3.3.1.1$^{3,7}$]decane;
3H-(4'r)-1'-azaspiro[5-(2-oxo-indolin-5-yl)-benzofuran-2,4']-tricyclo[3.3.1.1$^{3,7}$]decane;
3H-(4'r)-1'-azaspiro[5-(thiophen-3-yl)-benzofuran-2,4']-tricyclo[3.3.1.1$^{3,7}$]decane;
3H-(4'r)-1'-azaspiiro[5-(1H-pyrrolo[2,3-b]pyridin-5-yl)-benzofuran-2,4']-tricyclo[3.3.1.1$^{3,7}$]decane; or
3H-(4'r)-1'-azaspiro[5-(thieno[2,3-b]pyridin-5-yl)-benzofuran-2,4']-tricyclo[3.3.1.1$^{3,7}$]decane.

\* \* \* \* \*